(12) United States Patent
Nortman et al.

(10) Patent No.: US 6,276,032 B1
(45) Date of Patent: Aug. 21, 2001

(54) MECHANICAL FASTENING SYSTEM HAVING A PLURALITY OF ENGAGEMENT MEMBERS WHICH INCLUDE STALK MEMBERS

(75) Inventors: Brian Keith Nortman; Andrew Edsel Huntoon; Andrew Mark Long, all of Appleton; Patrick Robert Lord, Neenah; Gordon Allen Shaw, Greenville; Sang Van Tran; Paula Kay Zoromski, both of Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/491,070

(22) Filed: Jan. 25, 2000

(51) Int. Cl.[7] ....................................... A41F 1/00
(52) U.S. Cl. ............................................. 24/572.1
(58) Field of Search ......................... 24/572, 306, 442, 24/445, 446, 449, 452; 604/391

(56) References Cited

U.S. PATENT DOCUMENTS

| | | | |
|---|---|---|---|
| 3,408,705 | * 11/1968 | Kayser et al. ....................... 24/452 |
| 4,846,815 | * 7/1989 | Scripps ............................... 604/391 |
| 4,894,060 | * 1/1990 | Nestgard ............................. 604/391 |
| 5,369,852 | * 12/1994 | Higashinaka ....................... 24/446 |
| 5,586,372 | 12/1996 | Eguchi et al. . |
| 5,692,271 | 12/1997 | Provost et al. . |
| 5,884,374 | 3/1999 | Clune . |
| 5,897,545 | * 4/1999 | Kline et al. ...................... 604/391 X |
| 5,953,797 | * 9/1999 | Provost et al. ......................... 24/452 |
| 5,974,635 | * 11/1999 | Murasaki ......................... 24/452 X |
| 6,061,881 | 5/2000 | Takizawa et al. . |

FOREIGN PATENT DOCUMENTS 0 464 754 A1   1/1992  (EP) .

OTHER PUBLICATIONS

Patent Cooperation Treaty Search Report from the International Search Authority, International Application No. PCT/US 00/33006 dated Mar. 20, 2001.

* cited by examiner

*Primary Examiner*—Robert J. Sandy
(74) *Attorney, Agent, or Firm*—Paul Yee

(57) ABSTRACT

An article (10), has a first article portion (12), a second article portion (14), and a fastener (36). The fastener secures the first article portion to the second article portion and includes at least one first fastener component (70), which is attached to the first portion of the article. A cooperating, second fastener component (72) is mechanically interengageable with the first fastener component (70) and is attached to the second portion of the article (14). The first fastener component (70) includes a plurality of engagement members (56) having a first quantity of engageable stalk members (94).

20 Claims, 23 Drawing Sheets

MECHANICAL FASTENING SYSTEM HAVING A PLURALITY OF ENGAGEMENT MEMBERS WHICH INCLUDE STALK MEMBERS

FIELD OF THE INVENTION

The present invention relates to fastening systems for garments and other articles. More particularly, the present invention relates to interlocking, mechanical-type fastening systems which can be employed with disposable articles, such as gowns, diapers, incontinence garments and the like.

BACKGROUND OF THE INVENTION

Conventional disposable absorbent articles have typically employed adhesive fastening tapes for securing the article on a wearer. Such articles have also been constructed with interengaging mechanical fasteners, such as snaps, buckles, and hook-and-loop fasteners. Particular articles have included a fastening system which has extended along substantially the entire length of an ear section of the article. Other fastening systems have included strips or segmented sections of adhesive which have been arranged to extend along a portion of the length of the article ear section. In still other systems, the strips or segmented sections have been composed of selected mechanical fastener components, such as individual sections of hook material or loop material. Additionally, combinations of adhesive fasteners and mechanical fasteners have been employed.

Conventional mechanical fasteners have been composed of hook-and-loop fasteners, and various types of hook materials, such as inverted-J shaped, T-shaped and generally mushroom-shaped hooks have been employed. Such conventional fastening systems have also employed tapered fastening tabs where the attaching area on the user's end is relatively wide at its inboard region adjacent the longitudinally extending sides of the diaper, and is tapered to a more narrow width at its more remote distal end. Still other fastener tabs have incorporated bell-shaped fastening areas where the attaching area on the user's portion of the tab is shaped to be relatively narrow at an inboard region adjacent the longitudinally extending sides of the diaper, and to be wider at its more remote distal end.

Conventional fasteners and fastening systems, such as those described above, have not provided adequate levels of reliable securement and ease of unfastening. The conventional fastening systems have not provided a sufficient capability to accommodate the stresses imposed on the article by a wearer, while also providing a desired ease of unfastening after the article has been worn. When constructed and arranged to generate the desired levels of reliable securement, the conventional fasteners have been excessively difficult to unfasten for inspection or removal of the worn article. The difficulty can become especially apparent with mechanical fasteners after the fasteners have been in use for an extended period of time. As a result, the conventional fastening systems have not provided desired combinations of comfort, ease of fastening, strong securement, and ease of unfastening.

BRIEF DESCRIPTION OF THE INVENTION

Generally stated, the present invention provides a distinctive article, having a lengthwise longitudinal direction, and a lateral cross-direction. The article has a first article portion, a second article portion, and at least one fastener for securing the first article portion to said second article portion. The fastener includes at least one first fastener component attached to the first portion of the article, and a cooperating, second fastener component. The second fastener component is mechanically engageable with the first fastener component, and is attached to the second portion of the article. In a particular aspect, the first fastener component can include a plurality of engagement members having a first quantity of engageable stalk members.

In another aspect, the engagement members can include a first quantity of attachment members having engageable, attachment head elements. In further aspects, the first fastener component can include a first engagement section and a second engagement section. The first engagement section can include a first plurality of engagement members having a first quantity of engageable stalk members, and the second engagement section can include a second plurality of engagement members having a second quantity of engageable stalk members.

The incorporation of the various aspects of the fastening system of the invention can provide improved securement with greater resistance to premature pop-opens, and can also provide improved fit, greater comfort, and reduced irritation of the wearer's skin. The distinctively configured fasteners of the invention can advantageously provide an improved combination of properties, such as an improved combination of relatively high shear force engagement and relatively low peel force engagement. The various aspects of the invention can provide a fastening system having greater reliability and improved securement without generating excessive irritation, and can provide improved ease of unfastening for inspection and removal of the article.

BRIEF DESCRIPTION OF THE DRAWINGS

The present invention will be more fully understood and further advantages will become apparent when reference is made to the following detailed description of the invention and the drawings, in which:

FIG. 12A representatively shows an expanded, schematic cross-sectional view of the fastener of FIG. 12;

FIG. 22A representatively shows an expanded, schematic cross-sectional view of the fastener of FIG. 22.

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

Figure 1:
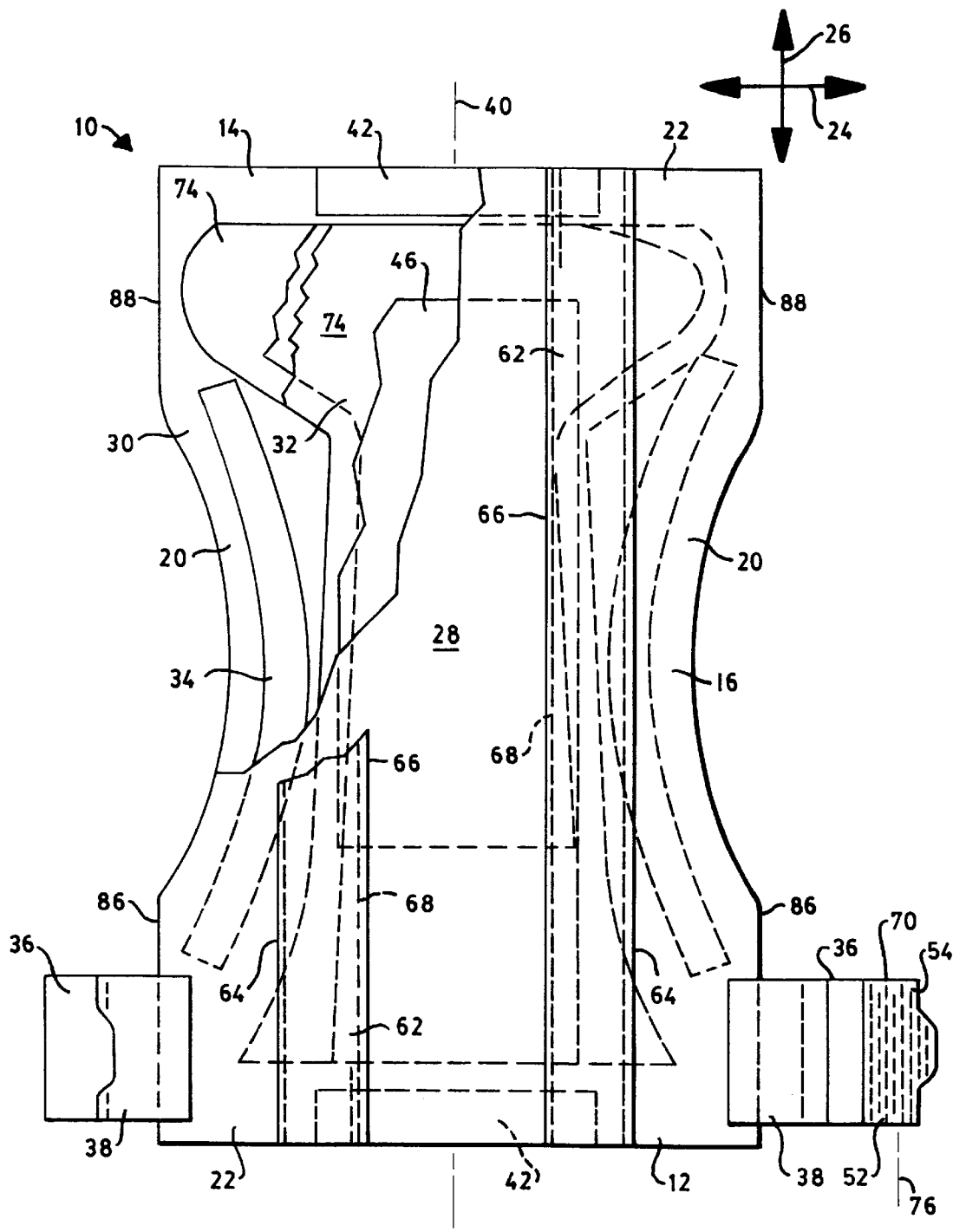
FIG. 1 representatively shows a partially cut-away, top view of an inward side of a diaper article which incorporates the fastening system of the invention.
Figure 2:
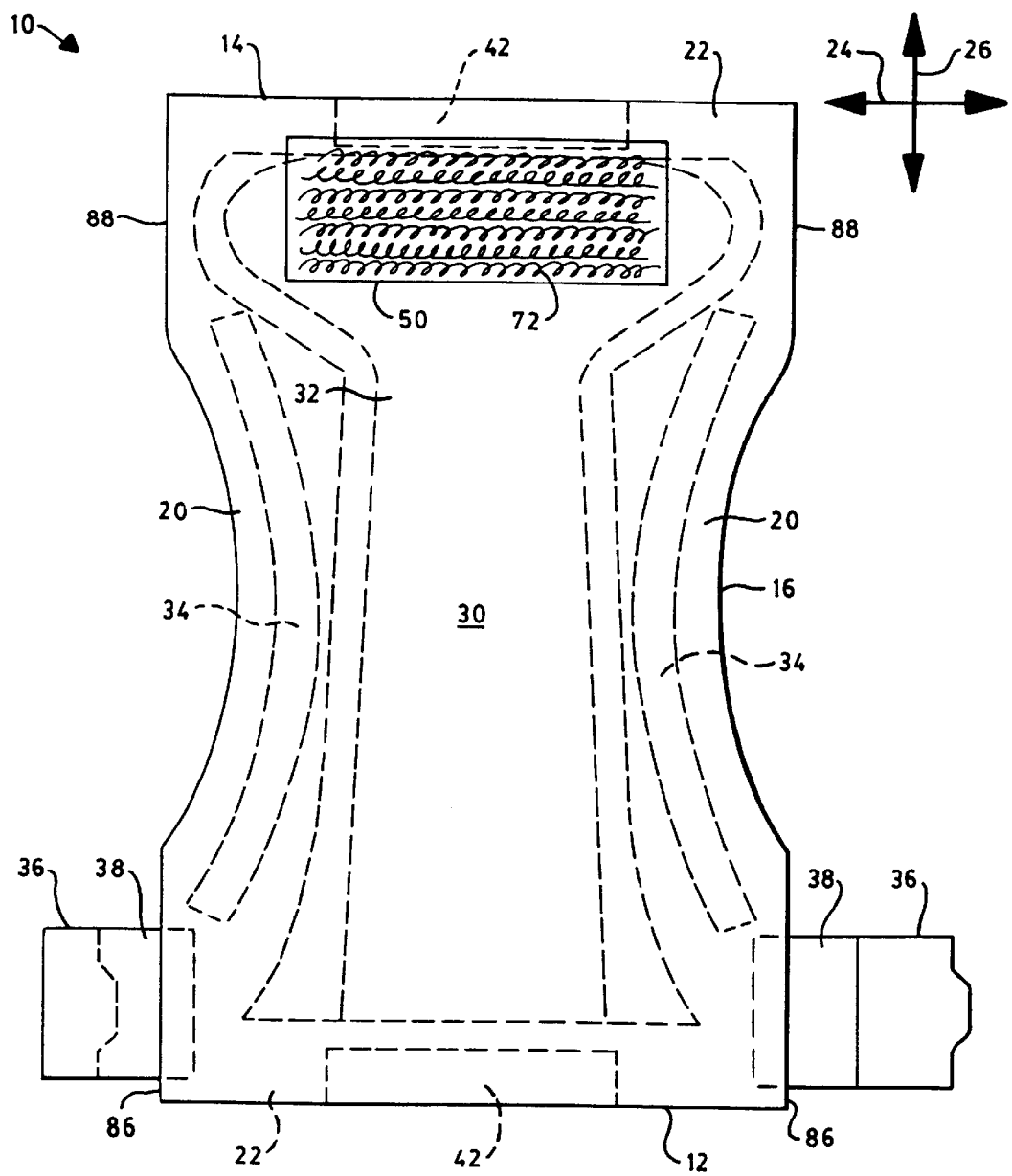
FIG. 2 representatively shows a top, plan view of an outward side of a diaper article which incorporates the fastening system of the invention.
Figure 3:
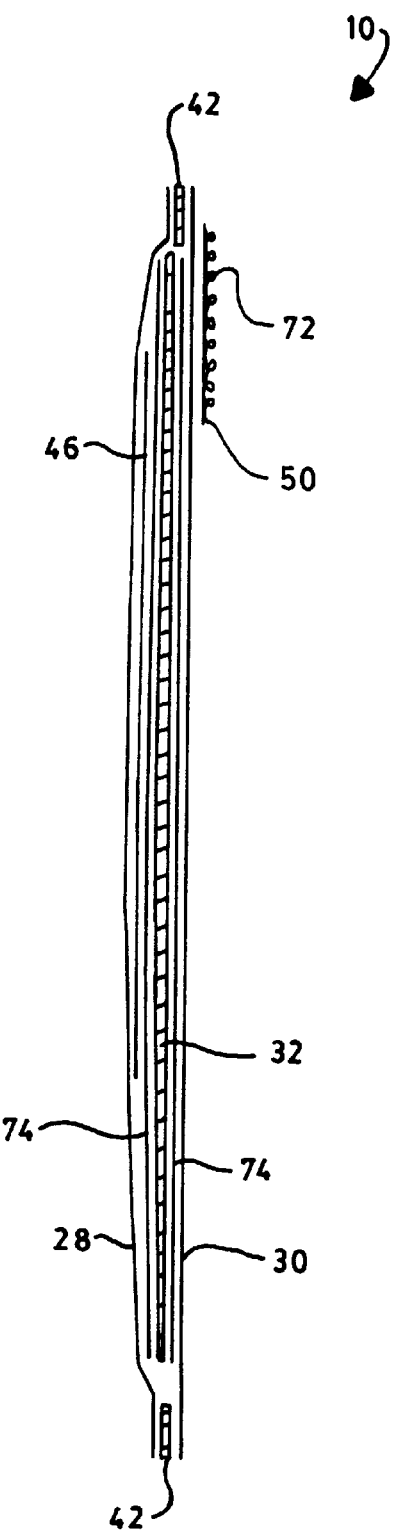
FIG. 3 representatively shows a schematic, longitudinal cross-sectional view of the article illustrated in FIG. 1.

With reference to FIGS. 1, 2 and 3, an article, such as the representatively shown diaper 10, has a lengthwise, longitudinal direction 26, a transverse, lateral cross-direction 24, and a longitudinally extending medial line 40. The article includes a first article portion 12, such as a first waistband portion, and a second article portion 14, such as a second waistband portion, and at least one fastener, such as provided by a fastener tab 36. The fastener secures the first article portion to the second article portion and includes at least one first fastener component 70, such as a hook component, which is attached to the first portion of the article. At least one cooperating, second fastener component 72, such as a loop component, is mechanically interengageable with the first fastener component 70 and is attached to the second portion of the article. In a particular aspect, the first fastener component 70 can include a plurality of engagement members 56 having a first quantity of engageable stalk members 94 (e.g. FIG. 8).

In other aspects of the invention, the plurality of engagement members 56 can also include a first, primary quantity of attachment members 93, each of which has a corresponding attachment head element 60.

In a further aspect, the first fastener component 70 can include a first engagement section 52 having a first plurality of engagement members with a first quantity of stalk members 94, and at least a second engagement section 54 having at least a second plurality of engagement members with a second quantity of stalk members.

In desired arrangements, the second quantity of stalk members differs from the first quantity of stalk members. In more particular arrangements, the second quantity of stalk members can be greater than the first quantity of stalk members.

In still other aspects, the first plurality of engagement members 56 can include the first quantity of engageable stalk members 94 combined with a first quantity of attachment members 93. The second plurality of engagement members can include the second quantity of engageable stalk members combined with a second quantity of attachment members. In desired configurations the attachment members can include attachment hook elements.

In other configurations of the invention, the first fastener component 70 can include additional engagement sections with additional distributions of engagement members. Each of the engagement sections can thereby provide a different distribution of engagement members having a different combination of stalk members and attachment members.

Additionally, each of the engagement sections can provide selected, different engagement forces. For example, the second engagement section 54 can provide a different engagement force, as compared to the first engagement section 52. In particular arrangements, the second engagement section can provide a greater or lesser peel force value than said first engagement section. In other arrangements, the second engagement section may provide a greater or lesser shear force value than said first engagement section.

In the various configurations of the invention, the attachment members in the first engagement section 52 can be substantially the same as, or different than the attachment members in the second engagement section 54. In addition, a fastener transition region 76 may be located between laterally adjacent regions of the first and second engagement sections 52 and 54. The first engagement section 52 may be positioned laterally inboard from the second engagement section 54 and relatively closer to the article medial line 40. Accordingly, the second engagement section 54 may be positioned relatively outboard from the first engagement section 52 and located relatively farther from the medial line. Optionally, the appointed first engagement section 52 may be positioned laterally outboard from the appointed second engagement section 54.

Figure 20:
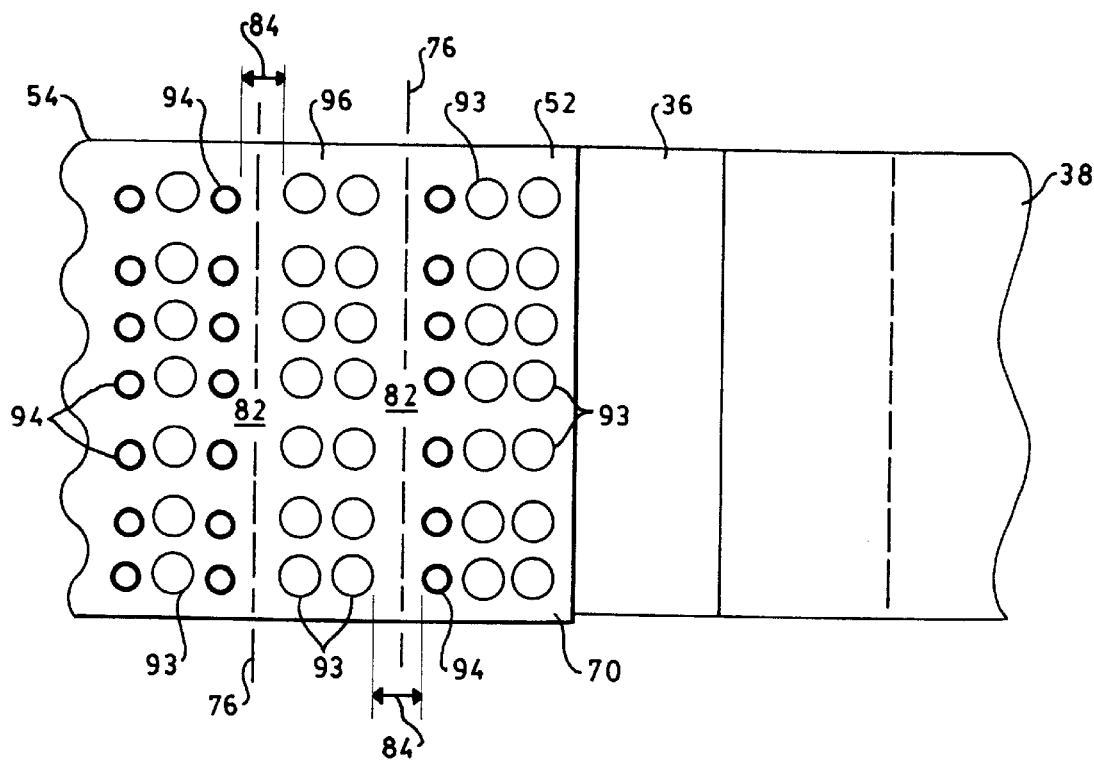
FIG. 20 representatively shows a schematic, top plan view of a fastener having three engagement sections, with each engagement section having a corresponding combination and distributional array of attachment members and stalk members, and with each engagement section having a strip configuration.
Figure 20A:
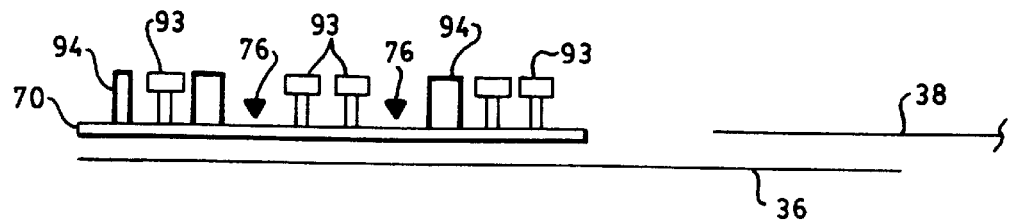
FIG. 20A representatively shows an expanded, schematic cross-sectional view of the fastener of FIG. 20

In other aspects, the article of the invention can have a first fastener component 70 which includes at least a third engagement section 96 (e.g. FIGS. 20 and 20A). The third engagement section can have a third plurality of engagement members which include a third quantity of stalk members. Additionally, the third engagement section can have a third quantity of attachment members.

As representatively shown, the fastening system can provide the at least one first fastener component 70 in a configuration which is operatively connected and attached to a lateral side section 86 of a first waistband portion 12 of the article, and can provide the cooperating, second fastener component 72 in a configuration which is operatively connected and attached to an appointed section of the second waistband portion 14 of the article. Desirably, at least one first fastener component 70 is attached to at least one lateral side section 86 of the first waistband portion 12. Optionally, the at least one first fastener component 70 can be attached to at least one lateral side section 88 of the second waistband portion 14, and the cooperating, second fastener component 72 can be attached to an appointed section of the first waistband portion 12. In desired configurations, at least one first fastener component 70 is attached to each of the two, laterally opposed side sections of the selected waistband portion.

The distinctive aspects of the present invention (individually and in combination) can advantageously help to better maintain the desired fit around the wearer. For example, the aspects of the invention can help reduce the sagging and drooping of the crotch region of the garment, and can help reduce rollover and drooping at the waist region. The incorporation of the various aspects of the fastening system of the invention can provide improved securement with greater resistance to premature pop-opens, and can also help provide improved fit, greater comfort and reduced irritation of the wearer's skin. The distinctively configured engagement zones and/or attachment members can provide a distinctive combination of high engagement areas for greater securement and reliability, and predetermined areas of relatively lesser engagement for greater ease in the unfastening and removal of the article from a wearer. In particular aspects, the amounts of peel strength and/or shear strength in selected areas can be controlled to provide desired combinations of securement. In other aspects, the distal or outboard, terminal end of the fastener tab can be more easily found, and can be more easily unfastened without employing a substantially unsecured finger lift tab.

The article of the invention can, for example, be a garment provided by the representatively shown disposable diaper 10. In desired configurations, the first article portion can provide a first waistband portion, such as the shown back waistband portion 12, and the second article portion can provide a second waistband portion, such as the shown front waistband portion 14. The article can additionally have an intermediate or crotch portion 16 which interconnects between the first and second waistband portions 12 and 14, respectively. The article can further include a backsheet layer 30, a liquid permeable topsheet layer 28 connected and assembled in facing relation with the backsheet layer, and an absorbent structure, such as a structure which includes absorbent body 32. The absorbent structure is sandwiched between the backsheet and topsheet layers, and is operably held therebetween. An operative fastening system, such as the shown system having fasteners 36, is typically constructed and arranged to interconnect the first waistband portion 12 with the second waistband portion 14 to hold the article on a wearer. The fastening system can be operatively configured to join the first, back waistband portion 12 in an overlapping relation with the second, front waistband portion 14 in a back-to-front arrangement to thereby encircle the wearer's body and hold the diaper secure on the wearer during use. Optionally, the fastening system can employ fasteners 36 which are configured to join the front waistband portion 14 in an overlapping relation with the back waistband portion 12 in a front-to-back arrangement to secure the diaper. In such optional arrangements, the front waistband region may be identified as the first waistband portion 12 and the rear waistband region may be identified as the second waistband portion 14.

The front waistband section 14 of the representatively shown diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article can also have an appointed fastener landing zone member 50 which is disposed on the outward surface of the article. In the configuration shown in FIGS. 1 and 2, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

FIGS. 1 and 2 show typical plan views of the representative disposable diaper 10 in its generally flat-out, uncontracted state (i.e., with substantially all elastic induced gathering and contraction removed). In FIG. 1, portions of the structure are partially cut away to more clearly show the interior construction of the diaper article, and the bodyside surface of the diaper which contacts the wearer is facing the viewer. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article are configured to face away from the wearer's body when the article is placed about the wearer.

With reference to FIGS. 1, 2 and 3, the diaper 10 can typically include a porous, liquid permeable topsheet 28; a substantially liquid impermeable backsheet 30; an absorbent body structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with an appointed storage or retention portion of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993 which corresponds to PCT document WO95/16425 published Jun. 22, 1995. Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995 in U.S. Pat. No. 5,540,796 entitled A PROCESS FOR ASSEMBLING ELASTICIZED EAR PORTIONS by D. Fries, which issued Jul. 30, 1996, and in U.S. Pat. No. 5,595,618 entitled AN ASSEMBLY PROCESS FOR A LAMINATED TAPE by D. Fries, which issued Jan. 21, 1997. The disclosures of the above-described documents are incorporated herein by reference in a manner that is consistent (not in conflict) herewith.

The diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated fluid surges typically occur in the diaper or other disposable absorbent article.

The backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present disclosure, the term "flexible" refers to materials which are compliant and which will readily conform to the general shape and contours of the wearer's body. Backsheet 30 prevents the exudates contained in absorbent body 32 from wetting articles, such as bedsheets and overgarments, which contact diaper 10. In particular embodiments of the invention, backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, non-woven fabric layer laminated to an appointed facing surface of a polymer film layer which may or may not be gas-permeable. Ordinarily, the fabric layer is attached to an outward-facing surface of the polymer film layer. Other examples of fibrous, cloth-like backsheet materials can comprise a stretch-thinned or a stretch-thermal-laminate material composed of a 0.6 ml (0.015 mm) thick polypropylene blown film and a 0.7 ounce per square yard (23.8 gsm) polypropylene spunbond material (2 denier fibers).

In particular arrangements, a substantially liquid impermeable, vapor permeable backsheet layer may be a composite material which includes a vapor permeable film layer adhesively laminated to a spunbond layer. The vapor permeable film layer can be obtained from the Tredegar Film Products division of Tredegar Industries, Inc., under the tradename EXAIRE. The film layer can include 48–60 weight percent (wt %) linear low-density polyethylene and 38–50 wt % calcium carbonate particulates which may be uniformly dispersed and extruded into the film layer. The film layer can be stretched to have a thickness of about 0.7 mil (about 0.018 mm) and a basis weight of 16–22 grams per square meter ($g/m^2$). The spunbond layer can be adhesively laminated to the film layer, and can have a basis weight of about 27 $g/m^2$. The spunbond layer can be made using conventional spunbond technology, and can include filaments of polypropylene having a fiber denier of 1.5–3 dpf. The vapor-permeable film layer may be adhered to the spunbond layer using a pressure sensitive, hot melt adhesive at an add-on rate of about 1.6 $g/m^2$, and the adhesive can be deposited in the form of a pattern of adhesive swirls or a random fine fiber spray.

The liquid impermeable, vapor permeable backsheet layer may alternatively include a highly breathable stretch thermal laminate material (HBSTL). The HBSTL material can include a polypropylene spunbond material thermally attached to a stretched breathable film. For example, the HBSTL material may include a 0.6 osy (20.4 $g/m^2$) polypropylene spunbond material thermally attached to a 18.7 $g/m^2$ stretched breathable film. The breathable film may include two skin layers with each skin layer composed of 1–3 wt % EVA/catalloy. The breathable film may also include 55–60 wt % calcium carbonate particulates, linear low-density polyethylene, and up to 4.8% low density polyethylene. The stretched breathable film can include a thickness of 0.45–0.50 mils (0.011–0.013 mm) and a basis weight of 18.7 $g/m^2$. The spunbond layer can be thermally bonded to the breathable film, and can have a basis weight of about 20.4 $g/m^2$. The spunbond layer can have a fiber denier of 1.5–3 dpf, and the stretched breathable film can be thermally attached to the spunbond material using a "C-star" pattern which provides an overall bond area of 15–20%.

The various types of such materials have been employed to form the backsheet or outercover of HUGGIES disposable diapers, which are commercially available from Kimberly-Clark Corporation. The backsheet 30 typically provides the outer cover of the article. Optionally, however, the article may include a separate outer cover component member which is additional to the backsheet. The backsheet may also be embossed or otherwise provided with a pattern or matte finish to exhibit a more aesthetically pleasing appearance.

As mentioned, the backsheet 30 may include a microporous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. Another example of a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn.

In the various configurations of the invention, where a component such as the backsheet 30 or the containment flaps 62 are configured to be permeable to gas while having a resistance and limited permeability to aqueous liquid, the liquid resistant material can have a construction which is capable of supporting a selected hydrohead of water substantially without leakage therethrough. For example, desired materials can support a hydrohead of at least about 45 cm of water substantially without leakage therethrough. A suitable technique for determining the resistance of a material to liquid penetration is Federal Test Method Standard FTMS 191 Method 5514, 1978, or an equivalent thereof.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1 inch), to provide at least a portion of the side and end margins.

The topsheet 28 presents a body-facing surface which is compliant, soft feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics"is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% TRITON X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment mechanisms may also be employed to suitably interconnect, assemble and/or affix together the various other component parts of the articles which are described herein.

The absorbent body 32 provides an absorbent structure which can include a retention portion, such as the representatively shown absorbent pad composed of selected hydrophilic fibers and high-absorbency particles, for holding and storing absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix. The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, absorbent body structure 32 can include an overwrap, such as wrap sheet 74, which is placed immediately adjacent and around absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of absorbent body 32. Such a configuration of the wrap sheet can, for example, facilitate the formation of a substantially complete sealing and closure around the peripheral edges of absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 10 can also include a surge management layer 46 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. Pat. No. 5,486,166 entitled FIBROUS NONWOVEN WEB SURGE LAYER FOR PERSONAL CARE ABSORBENT ARTICLES AND THE LIKE by C. Ellis and D. Bishop, which issued Jan. 23, 1996 and U.S. Pat. No. 5,490,846 entitled IMPROVED SURGE MANAGEMENT FIBROUS NONWOVEN WEB FOR PERSONAL CARE ABSORBENT ARTICLES AND THE LIKE by C. Ellis and R. Everett, which issued Feb. 13, 1996 the entire disclosures of which are hereby incorporated by reference in a manner that is consistent herewith.

The leg elastic members 34 are located in the lateral side margins 20 of diaper 10, and are arranged to draw and hold diaper 10 against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10. Alternatively, elastic members 34 may extend the entire length of diaper 10, or any other length suitable for providing the arrangement of elastically contractible lines desired for the particular diaper design.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 by T. Wisneski et al. which issued May 5, 1987, the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 by Mormon which issued Jul. 13, 1993, the entire disclosure of which is hereby incorporated by reference in a manner that is consistent herewith.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 by P. VanGompel et al. which issued Jul. 3, 1990, the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30. Additionally, a second pair of ear regions may be included to extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

Diaper 10 can also include a pair of elasticized containment flaps 62 which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 by K. Enloe which issued Nov. 3, 1987, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. Pat. No. 5,562,650 entitled ABSORBENT ARTICLE HAVING AN IMPROVED SURGE MANAGEMENT by R. Everett et al., which issued Feb. 13, 1996 the disclosure of which is hereby incorporated by reference in a manner that is consistent herewith.

Still other configurations of the invention can include a combination component that provides an elasticized leg gusset and a corresponding containment flap along each side edge region of the absorbent article. Examples of such articles are described in U.S. Pat. No. 5,904,675 entitled AN ABSORBENT ARTICLE WITH IMPROVED ELASTIC MARGINS AND CONTAINMENT SYSTEM by D. Laux et al., which issued May 18, 1999 and U.S. Pat. No. 5,993,433 entitled ABSORBENT ARTICLE WITH ENHANCED ELASTIC DESIGN FOR IMPROVED AESTHETICS AND CONTAINMENT by R. G. St. Louis et al., which issued Nov. 30, 1999. The entire disclosures of these documents are hereby incorporated by reference in a manner that is consistent herewith.

In optional configurations of the invention, diaper 10 may include internal, elasticized, containment waist flaps, such as those described in U.S. Pat. No. 4,753,646 issued Jun. 28, 1988, to K. Enloe; and in U.S. Pat. No. 5,827,259 entitled AN ABSORBENT ARTICLE WITH IMPROVED WAIST ELASTIC AND CONTAINMENT SYSTEM by D. Laux et al., which issued Oct. 27, 1998; the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid. To provide a desired refastenable fastening system, diaper 10 can include one or more, appointed landing member regions or patches, such as provided by the representatively shown, primary landing member 50. The landing member can provide an operable target area for generating a releasable and re-attachable securement with at least one of the fastener tabs 36. In desired embodiments of the invention, the landing member patch can be positioned on the front waistband portion 14 of the diaper and located on the outward surface of the backsheet layer 30. Alternatively, the landing member patch can be positioned on an appointed inward surface of the diaper, such as the bodyside surface of the topsheet layer 28.

Particular arrangements of the invention can include one or more landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the landing member may be composed of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 24.

The various configurations of the invention can include at least one separately provided fastener tab 36 located at either or both of the lateral end regions 86 of the back waistband 12. Alternatively, the at least one separately provided fastener tab 36 can be located at either or both of the lateral end regions 88 of the front waistband 14. The representatively shown embodiment, for example, has a laterally opposed pair of the fastener tabs 36 with a one of the fastener tabs located at each of the distal side edges of the rear waistband 12. More particularly, each of the fasteners 36 is assembled and attached to project and extend from a corresponding, immediately adjacent ear region located at one of the opposed, lateral end regions 86 of the front waistband section 12.

The fastener tab 36 can have any operative shape. For example, the shape of the fastener tab may be rectangular, trapezoidal, sinusoidal, rectilinear, curvilinear or the like, as well as combinations thereof. The laterally outboard, terminal edge of the fastener tab may be rectilinear or curvilinear, and as representatively shown, the terminal edge may be contoured to provide a protruding finger tab region.

The fastener tab 36 can be composed of a substantially non-elastomeric material, such as polymer films or tapes, woven fabrics, nonwoven fabrics or the like, as well as combinations thereof. Optionally, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically interengage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems typically include attachment members having the form of a "hook" or hook-like, male component, and include a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 36, and can locate the cooperating, second fastener component on the appointed engagement surface of the appointed landing member 50. For example, with the representatively shown hook-and-loop fastener, the fastening component which is attached to the appointed mating or securing surface of the fastener tab 36 may include a hook type of mechanical engagement element, and the complementary fastening component, which is operably joined and attached to the appointed landing zone member 50 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 36, may include the loop type of mechanical fastening element; and the complementary, second fastening component, which is operatively joined and attached to the appointed landing zone member, can include the hook type of attachment members.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 which corresponds to U.S. Pat. No. 5,624,429 which issued Apr. 29, 1997, the entire disclosure of which is hereby incorporated by reference in a manner which is consistent herewith.

With reference to FIGS. 4, 4A, 5 and 5A, the appointed first fastener component 70 can include a material having attachment members (e.g. the shown prong-type members or mushroom-shaped members) which project away from a base or substrate layer 110. Each attachment member 56 can have a stem portion 58 with a distal end portion 44, and an attachment element 60 which is desirably disposed at the distal end region of its corresponding stem portion 58 to provide a primary attachment opening 78. The attachment members 56 can be substantially isotropic, non-isotropic, substantially symmetric, or non-symmetric, as well as combinations thereof. The attachment members 93 can include various types of attachment elements 60. For example, the attachment members can include hook members having various types or styles of attachment hook elements. The attachment hook elements can include prong-type elements, J-shape elements, T-shape elements, mushroom-cap elements, nail-head elements or the like, as well as combinations thereof. Accordingly, the various configurations of the invention can include a first fastener component 70 which includes attachment members composed of a combination of two or more hook styles. For example, the first fastener component can include a combination of J-style hook members and mushroom-style hook members.

The stem portion 58 of each attachment member has a fixed end region 43, and a distal end region 44 which, desirably, is contiguously joined with the fixed end region. The fixed end region of the stem portion is operably attached to the substrate layer 110, and the distal end region is operably attached to its corresponding, associated attachment element 60. The stem portion 58 is sufficiently rigid to maintain the appointed upright positioning and the appointed directional alignment of the attachment element 60 during the ordinary operation of the first fastener component in the fastener system. More particularly, the stem portion is sufficiently resistant to bending and twisting to operably maintain the desired upright positioning and directional alignment of the attachment element. The substrate layer 110 has a substrate thickness 112, an attachment member surface 114, and an opposed substrate mounting surface 116. The selected attachment members are attached to the substrate layer 110, and project away from the attachment member surface 114.

Figure 4A:
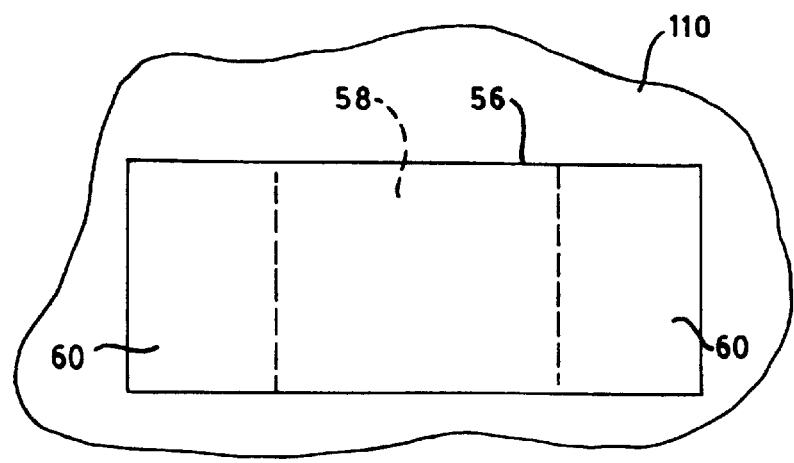
FIG. 4A representatively shows a top view of the attachment member of FIG. 4.
Figure 4:
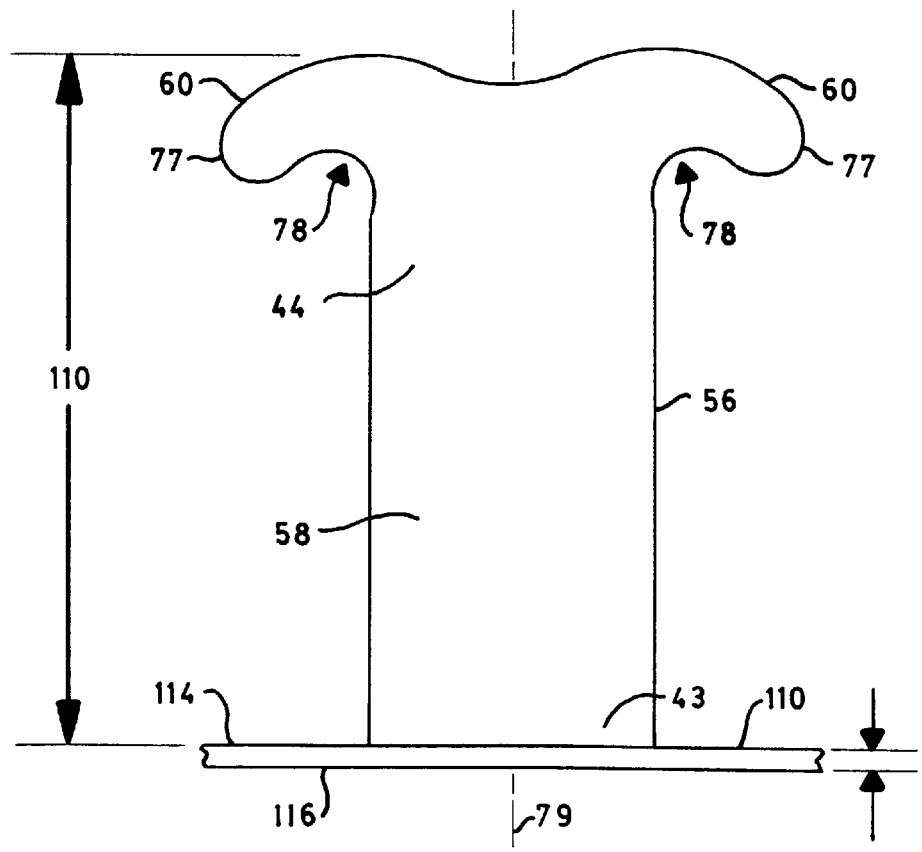
FIG. 4 representatively shows a side view of a non-isotropic, T-shape attachment member which can be employed with the present invention.
Figure 5A:
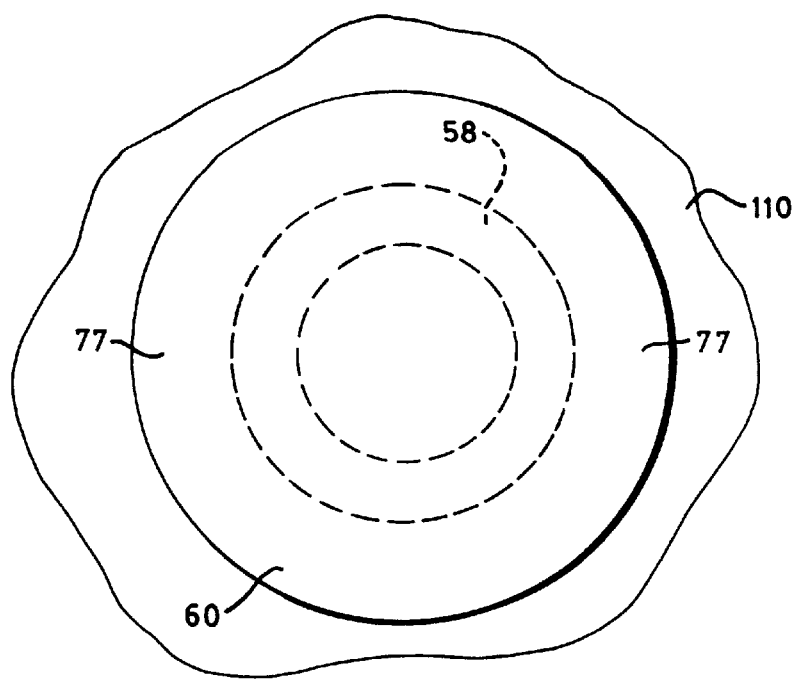
FIG. 5A representatively shows a top view of the attachment element on the attachment member of FIG. 5.
Figure 5:
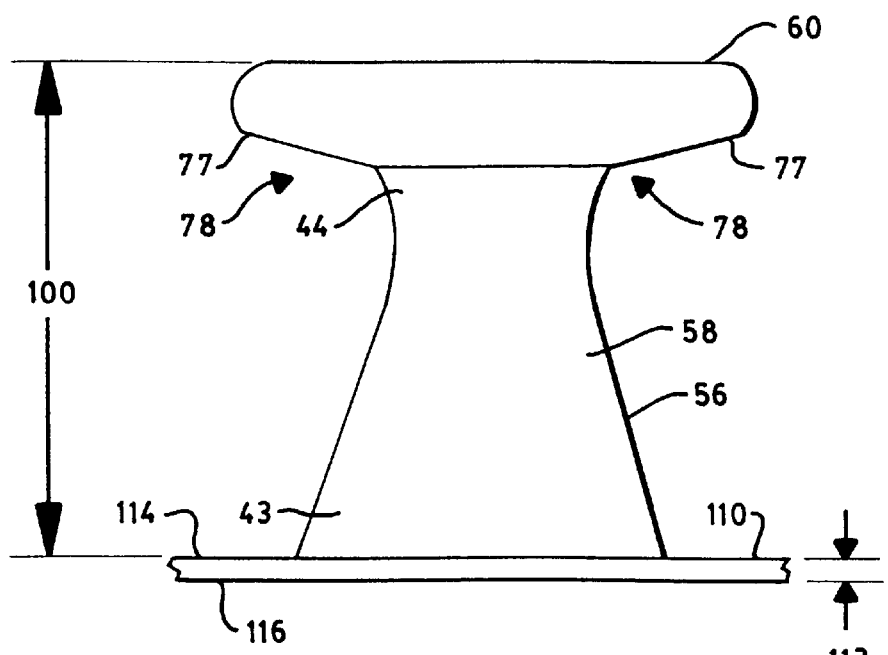
FIG. 5 representatively shows a side view of a substantially isotropic and symmetric hook-shape attachment member which can be employed with the present invention.

As representatively shown in FIGS. 4 and 4A, particular aspects of the invention may incorporate non-isotropic attachment members where the non-isotropic attachment members are configured to provide a directional or direction-dependent engagement with the cooperating second fastener component 72. Accordingly, with regard to a selected engagement parameter, the non-isotropic attachment member can provide a combination of two or more different fastening engagement values, with the value depending upon the direction along which the selected engagement parameter is measured. Thus, the non-isotropic (anisotropic) property of a fastener component pertains to the difference in one or more fastening properties that can be exhibited when the fastening component and associated attachment members are tensioned or otherwise stressed along different directions which are aligned substantially parallel to or generally along the extending area, "x-y" plane, of the fastening component. In particular, the attachment members can exhibit at least one bias direction along which a selected fastening property, such as peel force, shear force or the like, has a relatively different value. For example, the fastening property may have at least one bias direction along which a fastening property, such as peel force, shear force or the like, has a relatively maximal value. Similarly, the attachment members can exhibit at least one bias direction along which the selected fastening property has a relatively minimal value. The direction of maximal value may or may not be substantially opposite to the direction of relatively minimal value.

Thus, the non-isotropic attachment member may provide a greater (or lesser) shear force value or peel force value depending upon the direction along which the shear force or peel force value is determined. The non-isotropic feature may be generated by various suitable mechanisms, such as a difference in shape, size dimension, contour, length of projection, angle of projection, type of material, type of coating or other treatment, surface texture, surface topography, coefficient of friction, cohesion or the like, as well combinations thereof. The non-isotropic attachment member may have a limited degree of symmetry, such as a bilateral symmetry. Suitable non-isotropic attachment members can, for example, be provided by inverted-J-shaped or generally T-shaped attachment members. In another aspect, the first fastener component may include substantially isotropic attachment members, as representatively shown in FIGS. 5 and 5A. The isotropic attachment members have attachment elements which are substantially uniformly disposed with respect to a primary axis of the attachment member. Accordingly, the isotropic attachment members can exhibit substantially equal fastening properties in substantially all directions that are parallel to a plane that is generally established by the substrate layer of the first fastener component. For example, substantially isotropic attachment members may be provided by mushroom-shaped attachment members where the mushroom top is substantially symmetrically distributed about its upstanding stem portion and where the resulting attachment opening is similarly, substantially continuously distributed about its upstanding stem portion. In additional aspects, the fastening properties of the attachment members can be symmetric and equal in value with regard to selected predetermined sets of opposed directions. Examples of symmetric attachment members include T-shaped hook members. Other examples of suitable isotropic attachment members and symmetrical attachment members are representatively shown and described in U.S. patent application Ser. No. 09/156,185 entitled MECHANICAL FASTENING SYSTEM HAVING SECTIONS WITH ARRANGED ENGAGEMENT MEMBERS by A. Long et al. the entire disclosure of which is incorporated herein by reference in a manner that is consistent herewith.

Desirably, the presence of the operative attachment members can extend substantially continuously along approximately the entire length-wise dimension of the outboard terminal edge of the fastener tab. In optional configurations, a conventional, substantially non-engaging lift tab may be provided along a portion of the length-wise dimension of the outboard terminal edge of the fastener tab. The lift tab may be integrally formed from the appointed fastening component or fastener tab substrate, or may be a separately provided member which is assembled and affixed along the outboard terminal edge of the fastener tab.

Figure 6A:
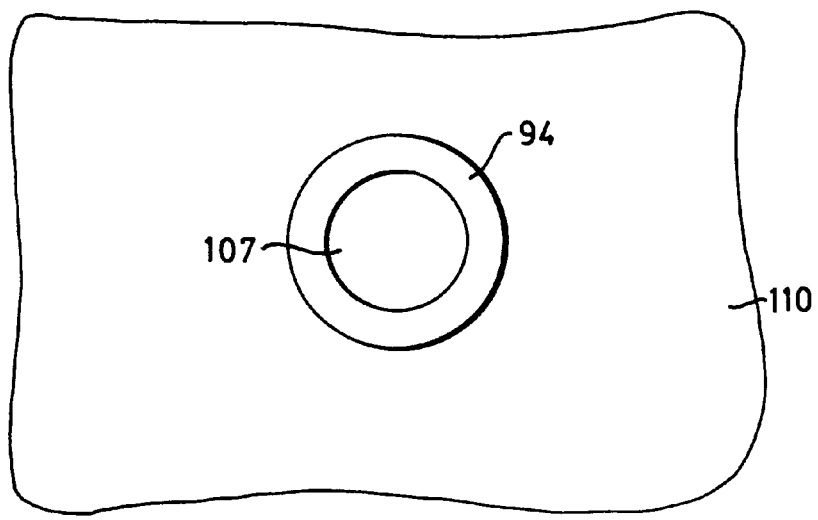
FIG. 6A representatively shows a top view of the engagement stalk member of FIG. 6.
Figure 6:
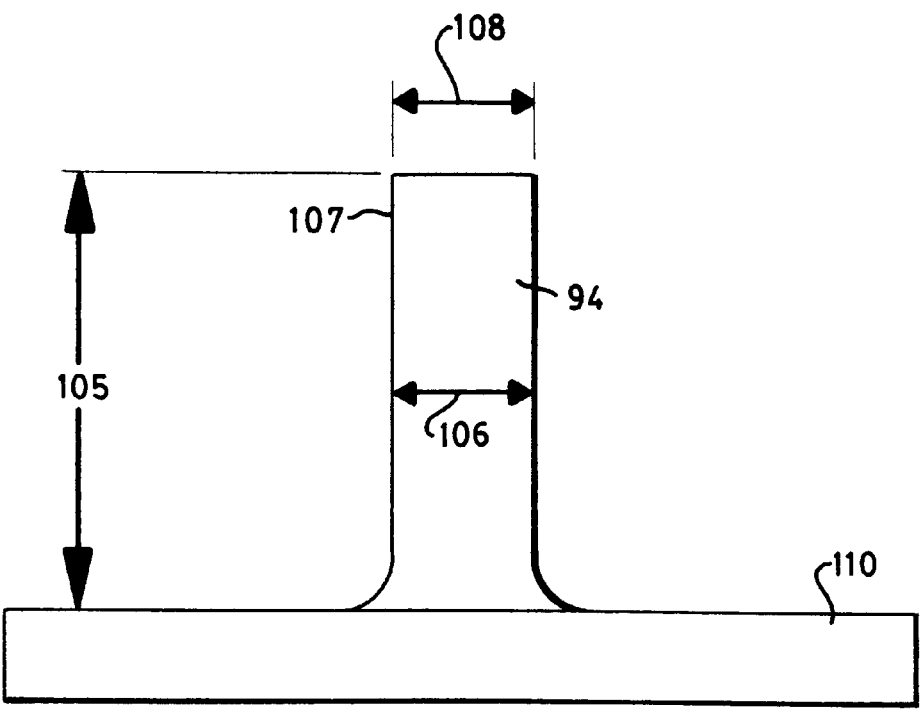
FIG. 6 representatively shows a side view of an engagement stalk member which can be employed with the present invention.
Figure 7A:
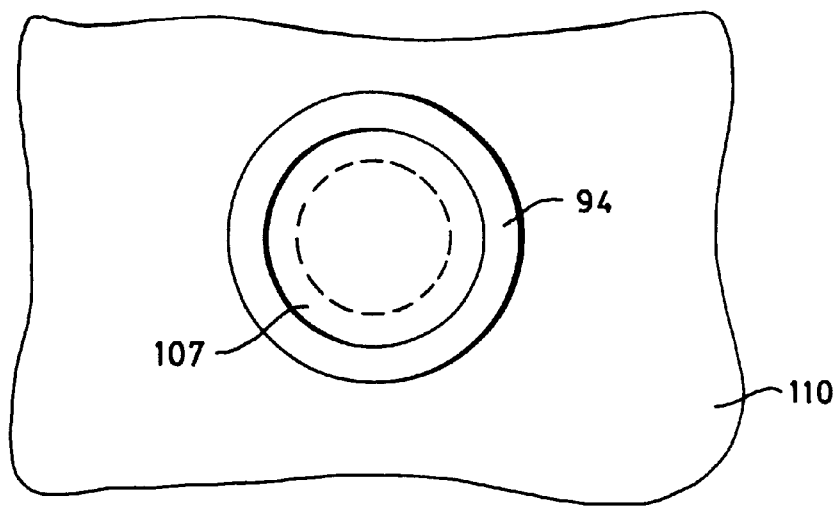
FIG. 7A representatively shows a top view of the engagement stalk member of FIG. 7.
Figure 7:
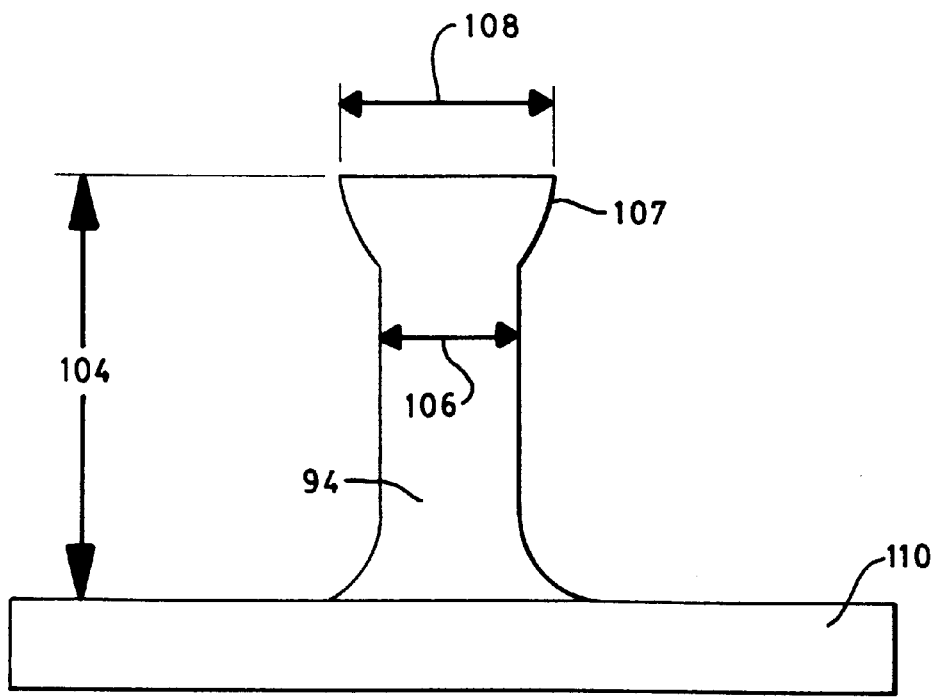
FIG. 7 representatively shows a side view of another engagement stalk member which can be employed with the present invention.

With reference to FIGS. 6 through 7A, each stalk member 94 can have stalk length 105, a stalk height 104, a stalk width 106 and a distal end portion 107. Additionally, each stalk member can have a selected shape along its length. The lengthwise shape can be substantially constant (e.g. FIG. 6), or may be varied and non-constant (e.g. FIG. 7). Accordingly, the stalk members may have substantially straight sides, tapered sides, sloping sides, contoured sides, as well as combinations thereof. Additionally, the distal end regions of the stalk members may have a "golf-tee", bulbous or otherwise expanded shape. With reference to FIGS. 6A and 7A, each stalk member can also have a selected cross-sectional shape, and in the shown arrangement, the stalk member has a substantially circular cross-sectional shape. Optionally, the cross-sectional shape may be oval, elliptical, oblong, rectilinear, polygonal or the like, as well as combinations thereof. In the representatively shown arrangements, the stalk members are substantially perpendicular to their associated and connected substrates 110. The stalk members may, however, be alternatively aligned with their lengthwise, central axes skewed at a selected tilt angle which is slanted away from the perpendicular.

Where the stalk member has tapered or sloped sides, the sides can have a selected draft angle. Where each stalk member is constructed in a mold cavity, for example, the draft angle can be an angle determined between an axis of the mold cavity and a sidewall of the mold cavity. In particular aspects, the draft angle can be up to about 15 degrees, and can alternatively be at least about 20 degrees, or more, to provide desired performance.

In other aspects, the distal end portion of the stalk member can have a maximum end-span 108 which is not more than a maximum of about 130% of the minimum width 106 of its corresponding stalk member. The end-span can alternatively be not more than about 115% of the minimum width 106 of its corresponding stalk member, and optionally, can be not more than about 104% of the minimum width 106 of its corresponding stalk member to provide improved effectiveness. While the invention does not contemplate a required minimum value for the end-span of the distal end portion of the stalk member, the end of the stalk member should be large enough, or otherwise configured to avoid excessive irritation to the wearer of the article.

If the end span is too large, the stalk member 94 can excessively interfere with the generation of the desired peel force value within its corresponding engagement section. Accordingly, the fastener system may not generate the desired combination of peel force and shear force. If the stalk end-span 108 is too small, the projecting distal ends of the stalk members may be excessively harsh and irritating.

For the purpose of determining the end-span percentage, the end-span will typically occur at or proximate the terminal, free end of the stalk member. Additionally, the minimum stalk width is a width dimension that is operatively engageable by a cooperating loop material. Accordingly, topographical features of the stalk member that would be over-spanned by a loop material, features such as surface holes, dents and grooves, would be ignored when ascertaining the effective, minimum width dimension. Typically the minimum width will occur at a location along the lengthwise, height dimension of the stalk member.

The determination of the end-span percentage that is provided by a particular stalk member can be determined by employing a projected side-view of the stalk member. Typically, the selected side-view is one which is expected to provide the maximum value for the end-span percentage. The measurements of end-span and the minimum width of the stalk member are taken with respect to the projection of the selected side-view onto an appropriate viewing surface.

With reference to FIG. 7, particular aspects of the invention can include stalk members 94 which have a stalk height 104 which is at least a minimum of about 0.025 cm. The stalk height can alternatively be at least about 0.04 cm, and optionally can be at least about 0.05 cm, or more, to provide improved performance.

In the various configurations of the invention, the attachment members in a selected engagement section can provide an average hook height value 100, and the stalk members in the selected engagement section can provide an average stalk height value which is a selected percentage of the average hook height value. For example, a selected engagement section can include stalk members having an average stalk height which is at least a minimum of about 10 percent of the average hook height value. The stalk height value can alternatively be at least about 30%, and optionally can be at least about 50% of the average hook height value to provide improved benefits. Additionally, the stalk members can provide an average stalk height value 104 which is not more than a maximum of about 97% of the average hook height value. The stalk height value can alternatively be not more than about 80%, and optionally can be not more than about 70% of the average hook height value to provide improved effectiveness.

In arrangements of other selected engagement sections, the stalk members can provide an average stalk height value which is up to about 105% of the average hook height value. The stalk height value can alternatively be up to about 125%, and optionally can be up to about 150% of the average hook height value to provide improved benefits. In further arrangements, the stalk members can provide an average stalk height value which is not more than a maximum of about 330% of the average hook height value. The stalk height value can alternatively be not more than about 250%, and optionally can be not more than about 200% of the average hook height value to provide improved effectiveness.

If the stalk height values are too small, the stalk members will not adequately provide the desired level of shear-force engagement with the cooperating, second mechanical fastener component 72. If the stalk height values are too large, the stalk members may present an array of harsh projections that can be unpleasant to the touch and can provide excessive irritation.

Figure 8:
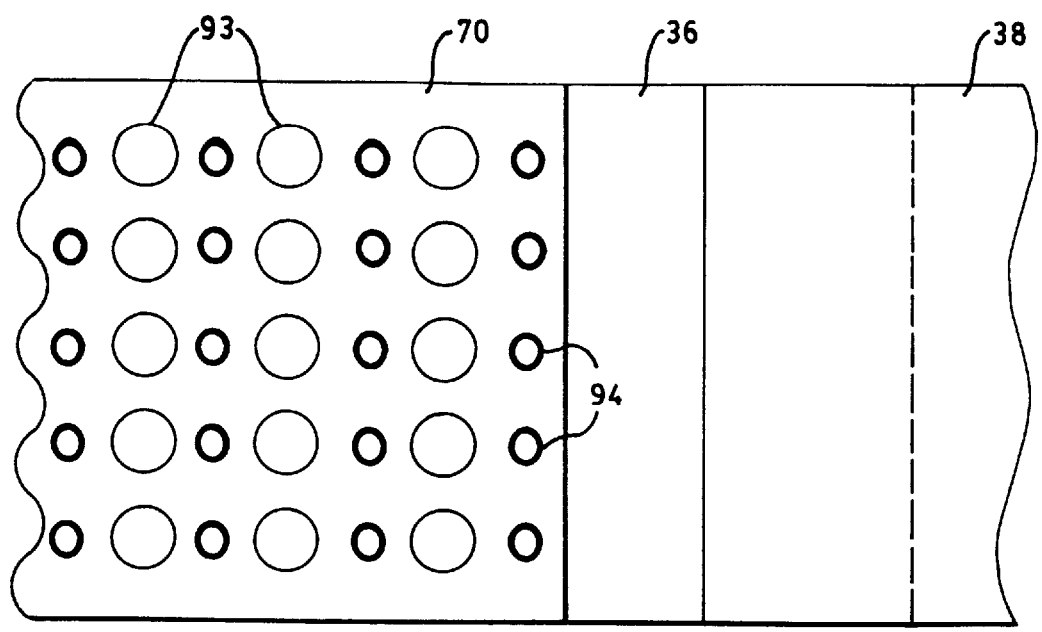
FIG. 8 representatively shows a schematic, top plan view of a fastener having a combination of engagement stalk members, and attachment members with nail-head attachment elements.
Figure 8A:
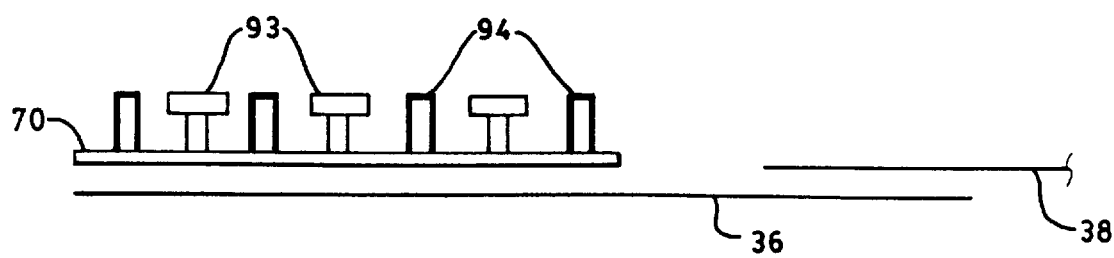
FIG. 8A representatively shows an expanded, schematic cross-sectional view of the fastener of FIG. 8.

With reference to FIGS. 8 and 8A, the first fastener component 70 includes a plurality of engagement members having at least a first quantity of engageable stalk members 94. Additionally, the first fastener component may include a first, primary quantity of attachment members 93 that have attachment head elements. Where the first fastener component 70 includes a combination of stalk members 94 and attachment members 93, the stalk members and attachment members may be uniformly or nonuniformly distributed across the area of the first fastener component. The distributions of the stalk members and attachment members may be in any desired pattern. For example, the stalk members and/or attachment members may be arranged along machine-direction lines, cross-direction lines, diagonal lines, curved lines, linear or curvilinear patterns, checkerboard patterns, or the like, as well as combinations thereof.

The various quantities, concentrations, distributions, combinations or other configurations of the stalk members and/or attachment members can be selected and arranged to generate desired combinations of peel force value and shear force value in the overall first fastener component 70. In addition, the various arrangements and configurations of the stalk members and/or attachment members can be selected to generate desired combinations of peel force value and shear force value in each individual engagement section of the first fastener component. Accordingly, each engagement section can be tailored to provide desired combinations of reliable securement and ease of fastening and unfastening.

The first mechanical fastener component 70 can include a plurality of engagement members 56 in which the number of individual stalk members 94 is at least a minimum of about 5 percent of the total number of engagement members 56 in the first fastener component. The number of individual stalk members can alternatively be at least about 10%, and optionally, can be at least about 15% of the total number of engagement members to provide improved performance. In other aspects, the number of individual stalk members can be not more than a maximum of about 97 percent of the total number of engagement members. The number of individual stalk members can alternatively be not more than about 65%, and optionally, can be not more than about 35% of the total number of engagement members to provide improved effectiveness.

If the percentage of stalk members is too low, the amount of peel force may be too high and the fastener system may be excessively difficult to disengage. If the percentage of stalk members is too large, the amount of peel force may be too low and the fastener system may be excessively susceptible to premature pop-opens.

In other aspects, the number of individual attachment members 93 can be a selected percentage of the total number of engagement members 56. Desirably, the number of attachment members 93 can be at least a minimum of about 3 percent of the total number of engagement members 56 in the first fastener component. The number of individual attachment members can alternatively be at least about 10%, and optionally, can be at least about 15% of the total number of engagement members to provide improved performance. In other aspects, the number of individual attachment members can be not more than a maximum of about 95 percent of the total number of engagement members. The number of individual attachment members can alternatively be not more than about 65%, and optionally, can be not more than about 35% of the total number of engagement members to provide improved effectiveness.

If the percentage of attachment members is too low, the fastener system may experience excessive pop-opens, or may be too easily opened by active infants. If the percentage of attachment members is too large, the fastener system may be too difficult to open, particularly after a period of extended use.

Figure 9:
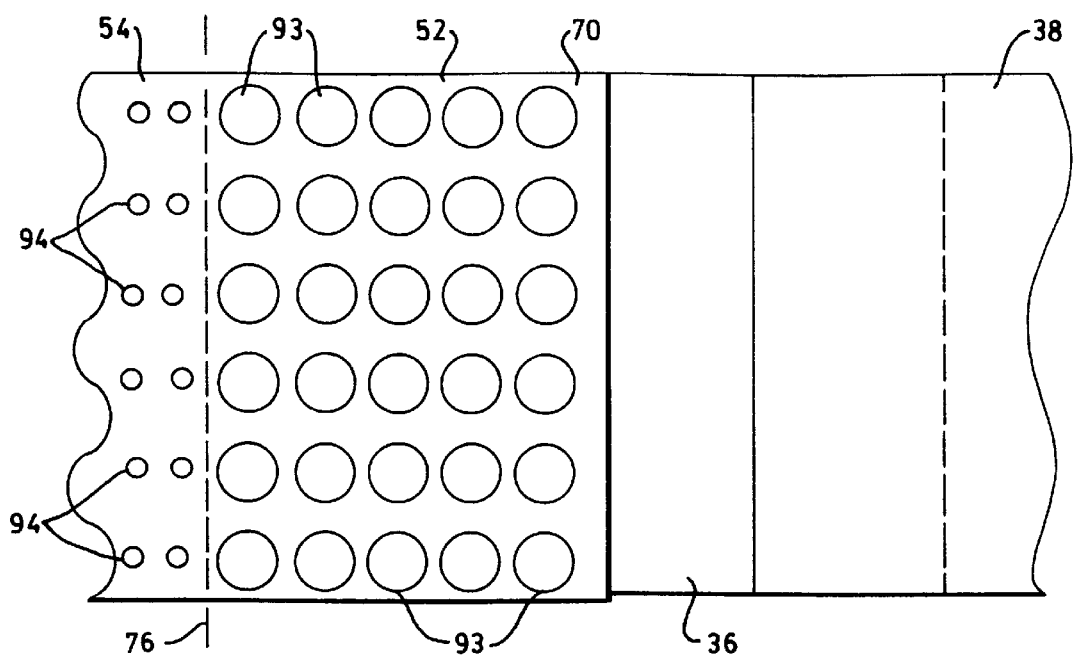
FIG. 9 representatively shows a schematic, top plan view of a fastener having a laterally inboard, first engagement section with an array of attachment members, and a laterally outboard, second engagement section with an array of stalk members.

With regard to particular aspects of the invention, the first fastener component 70 can further include a first engagement section 52 and a second engagement section 54 (e.g. FIG. 9). Each of the individual engagement sections can incorporate any desired combination of the engagement member distributions, engagement member concentrations, engagement member alignments, stalk member parameters, attachment member parameters, and the like, that are described in the present disclosure.

Figure 19:
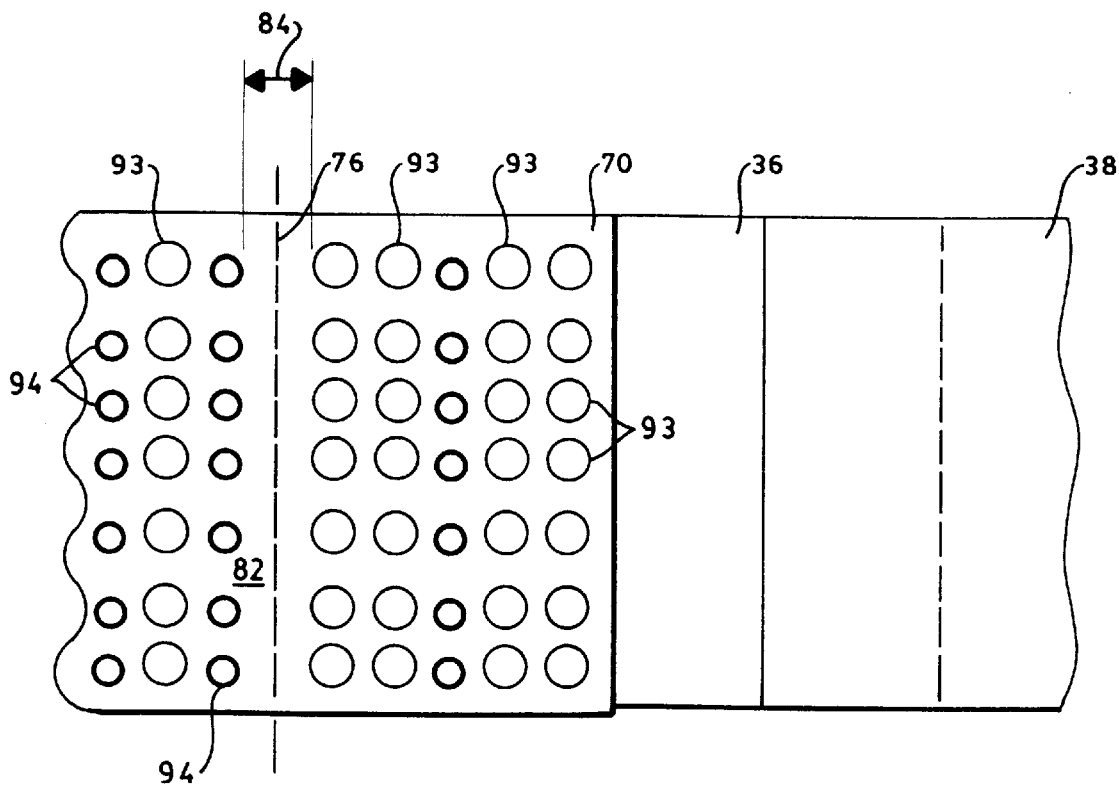
FIG. 19 representatively shows a schematic, top plan view of a fastener having a discrete spacing distance between a laterally inboard, first engagement section with a first combination of attachment members and stalk members, and a laterally outboard, second engagement section with a second combination of attachment members and stalk members.

In other configurations, the first fastener component 70 can further include two or more engagement sections with each engagement section having an individualized combination and/or distribution of engagement members (e.g. FIG. 19). For example, each engagement sections can include a different combination of stalk members and attachment members. As a result, each engagement section can provide a different, individualized combination of securement shear force and securement peel force. The differing engagement sections, such as sections 52 and 54, can also include distinctive combinations of features which provide desired combinations of fit, comfort and securement force.

Figure 9A:
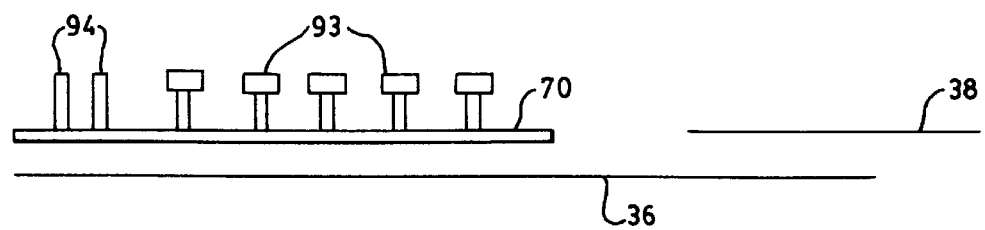
FIG. 9A representatively shows an expanded, schematic cross-sectional view of the fastener of FIG. 9.

With reference to the example illustrated in FIGS. 9 and 9A, the first engagement section 52 can include engagement members which are substantially 100% composed of attachment members 93. Additionally, the second engagement section 54 can include engagement members which are substantially 100% composed of stalk members 94. As a result, the relatively outboard engagement section can contribute a large amount of shear force engagement while also providing a relatively low level of peel force engagement. The relatively low peel force engagement can make it easier to locate and lift the outboard end of the first fastener component 70 for unfastening.

Figure 10:
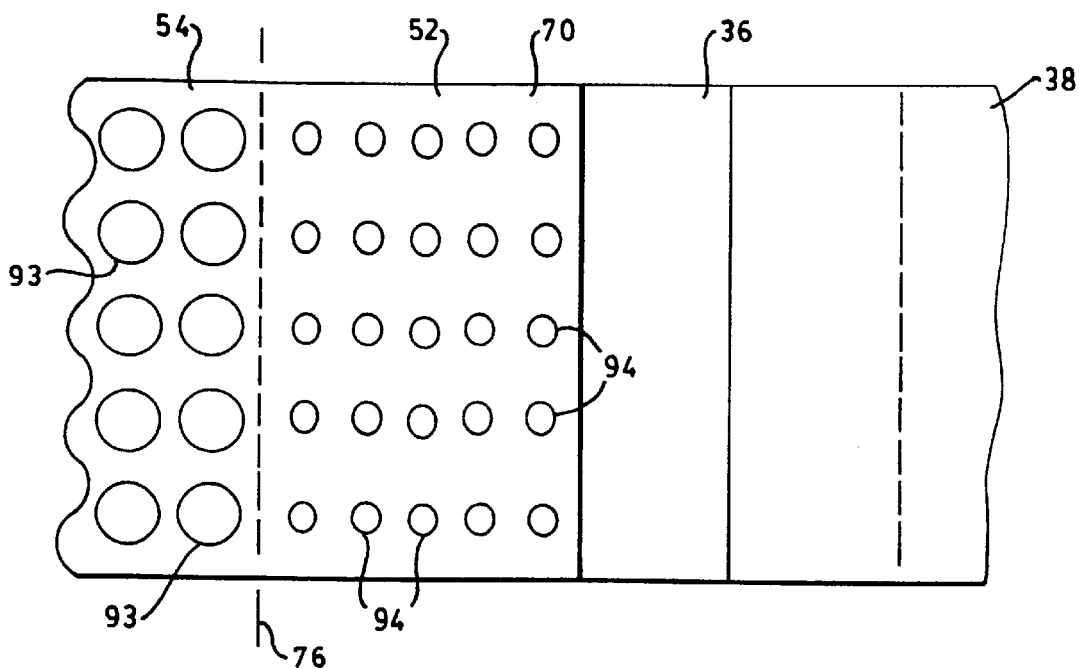
FIG. 10 representatively shows a schematic, top plan view of a fastener having a laterally inboard, first engagement section with an array of stalk members, and a laterally outboard, second engagement section with an array of attachment members.
Figure 10A:
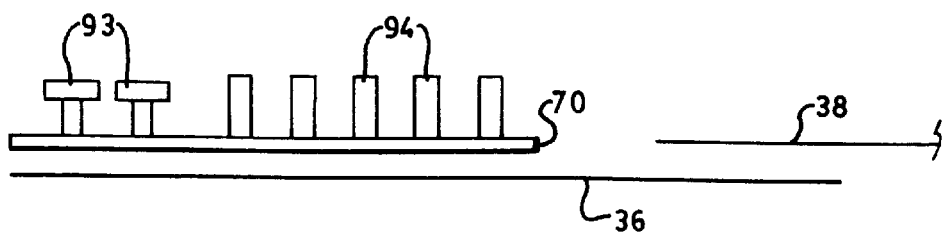
FIG. 10A representatively shows an expanded, schematic cross-sectional view of the fastener of FIG. 10.

With reference to FIGS. 10 and 10A, the inboard first engagement section 52 can include a quantity of engagement members which are substantially 100% composed of stalk members 94. Additionally, the relatively outboard second engagement section 54 can include a second quantity of engagement members which are substantially 100% composed of attachment members 93. As a result, the fastening system can provide a high shear force value in combination with a relatively low peel force value. At the same time, the concentration of the attachment members 93 in the outboard engagement section 54 can reduce the risk of undesired, premature disengagement of the first fastener component.

Figure 11:
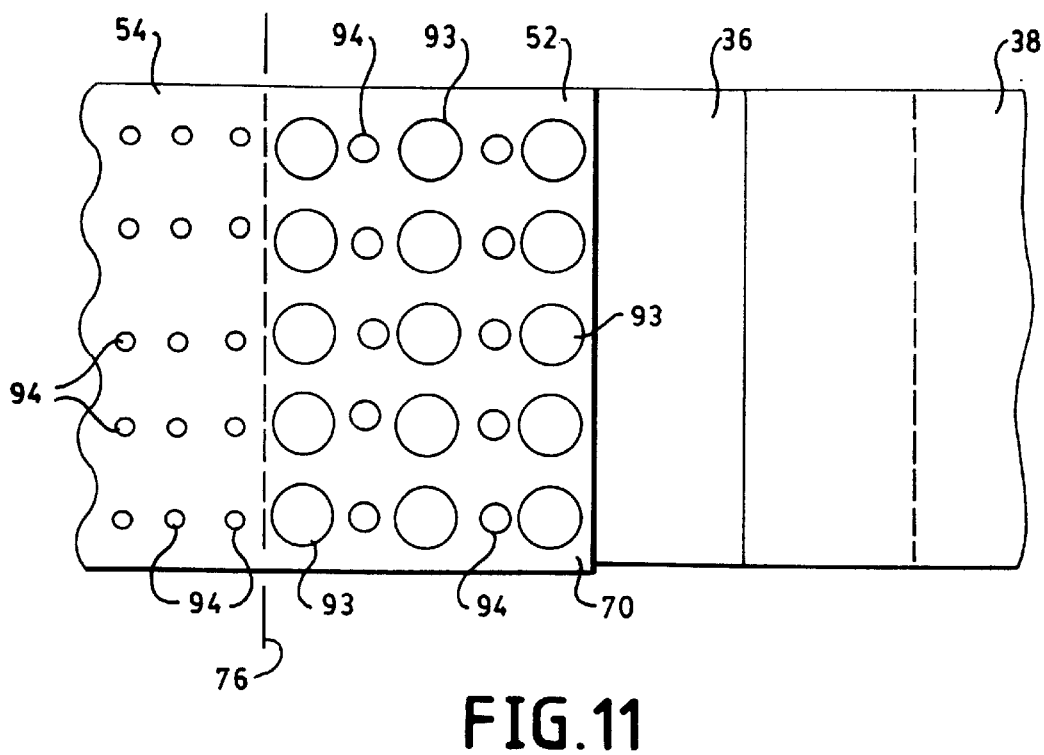
FIG. 11 representatively shows a schematic, top plan view of a fastener having a laterally inboard, first engagement section with a combination of attachment members and stalk members, and a laterally outboard, second engagement section with stalk members.
Figure 11A:
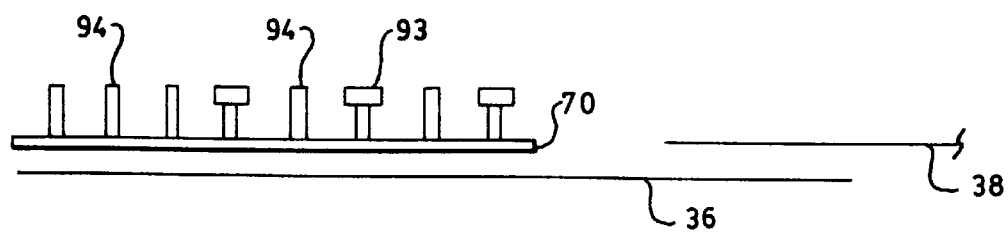
FIG. 11A representatively shows an expanded, schematic cross-sectional view of the fastener of FIG. 11.

With reference to FIGS. 11 and 11A, the first fastener component 70 can have a first engagement section 52 which includes a combination of attachment members 93 and stalk members 94. Additionally, the first fastener component can have a second engagement section 54 in which approximately 100% of the engagement members are stalk members 94. As a result, the outboard section 54 can contribute a high amount of shear force value while also providing a low peel force value in the second engagement section. This low peel force value can facilitate the finding and lifting of the distal end of the fastener tab 36. In addition, the inboard engagement section 52 can maintain a high shear force value while exhibiting a relatively lower peel force value. The lower peel force value can advantageously address the complaint of excessively strong attachment that can develop between the first fastener component and it's cooperating second fastener component after a period of extended wear.

Figure 12:
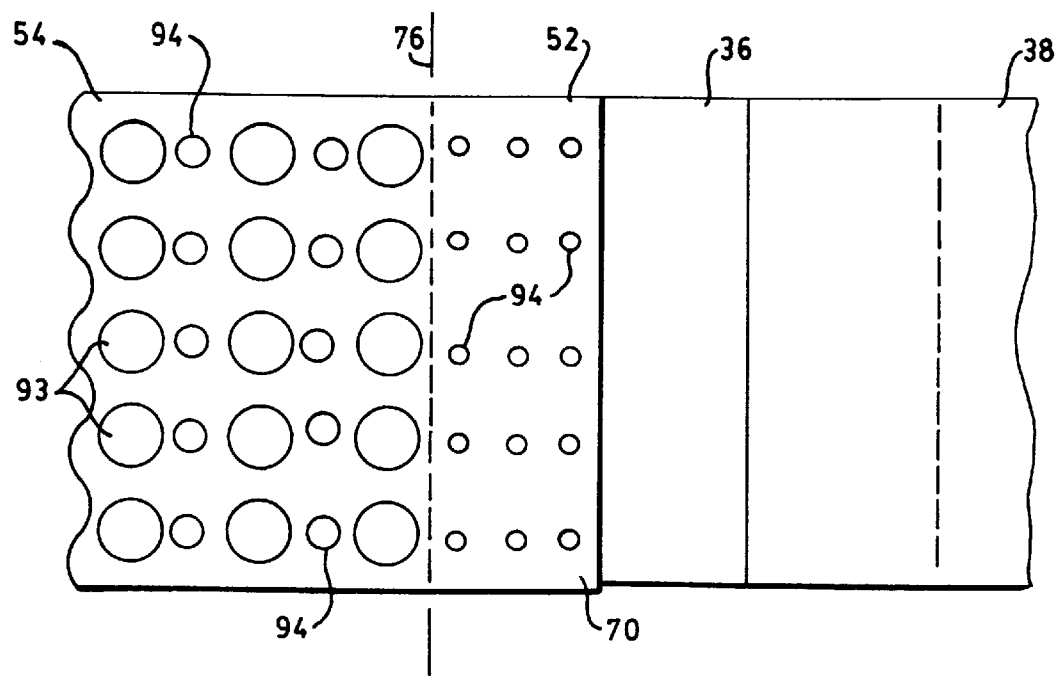
FIG. 12 representatively shows a schematic, top plan view of a fastener having a laterally inboard, first engagement section with stalk members, and a laterally outboard, second engagement section with a second combination of attachment members and stalk members.
Figure 12:
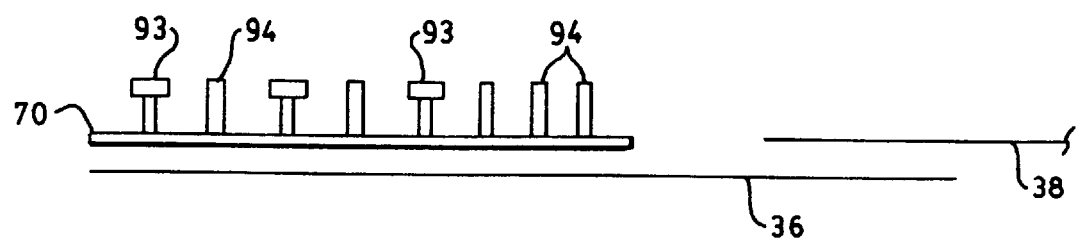

With reference to FIGS. 12 and 12A, the first fastener component 70 can include a first inboard engagement section 52 in which approximately 100% of the engagement members are provided by stalk members 94. Additionally, the second outboard engagement section 54 of the first fastener component can include engagement members composed of a combination of attachment members 93 and stalk members 94. As a result, the fastening system can be configured with a high, total shear force value while providing a relatively greater peel force value at the outboard engagement section 54 to lessen the risk of undesired, premature disengagement.

Figure 13:
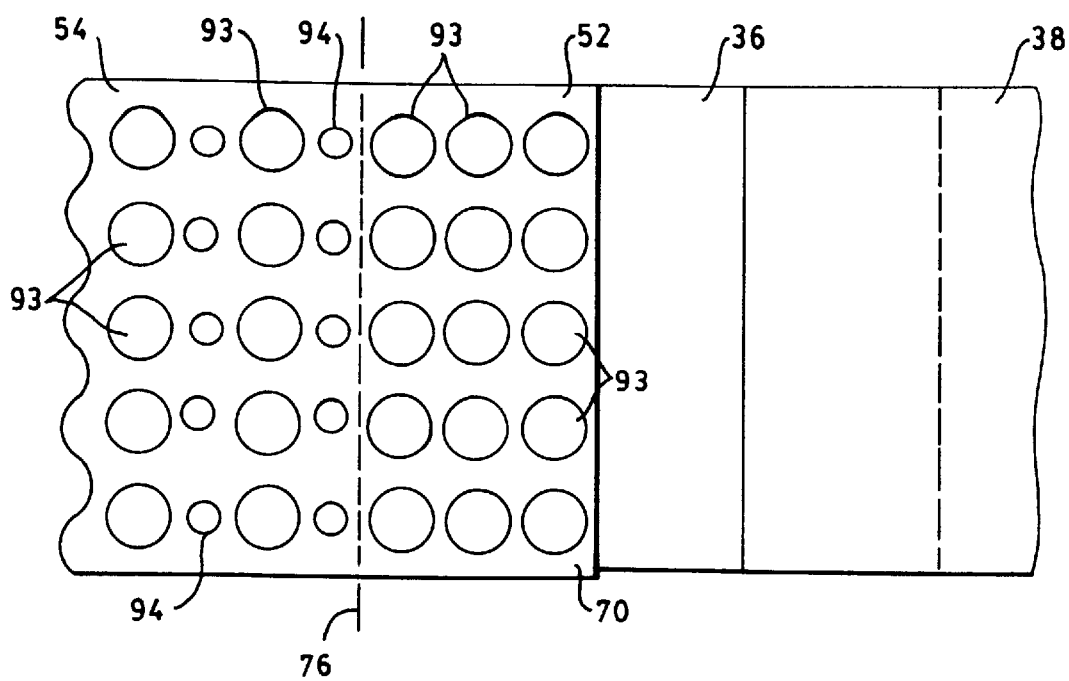
FIG. 13 representatively shows a schematic, top plan view of a fastener having a laterally inboard, first engagement section with attachment members, and a laterally outboard, second engagement section with a combination of attachment members and stalk members.
Figure 13A:
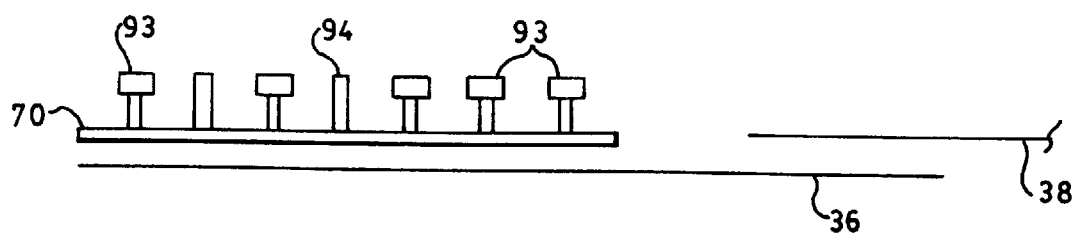
FIG. 13A representatively shows an expanded, schematic cross-sectional view of the fastener of FIG. 13.

With reference to FIGS. 13 and 13A, the first fastener component can have a first inboard engagement section 52 in which a substantially 100% of the engagement members are attachment members 93. Additionally, the first fastener component can have a second outboard engagement section 54 which includes a combination of stalk members 94 and attachment members 93. As a result, the fastening system can have an overall, high peel force value and an overall high shear force value, while having a relatively lower peel force value at the second engagement section 54 to provide an easier lifting of the second engagement section.

Figure 14:
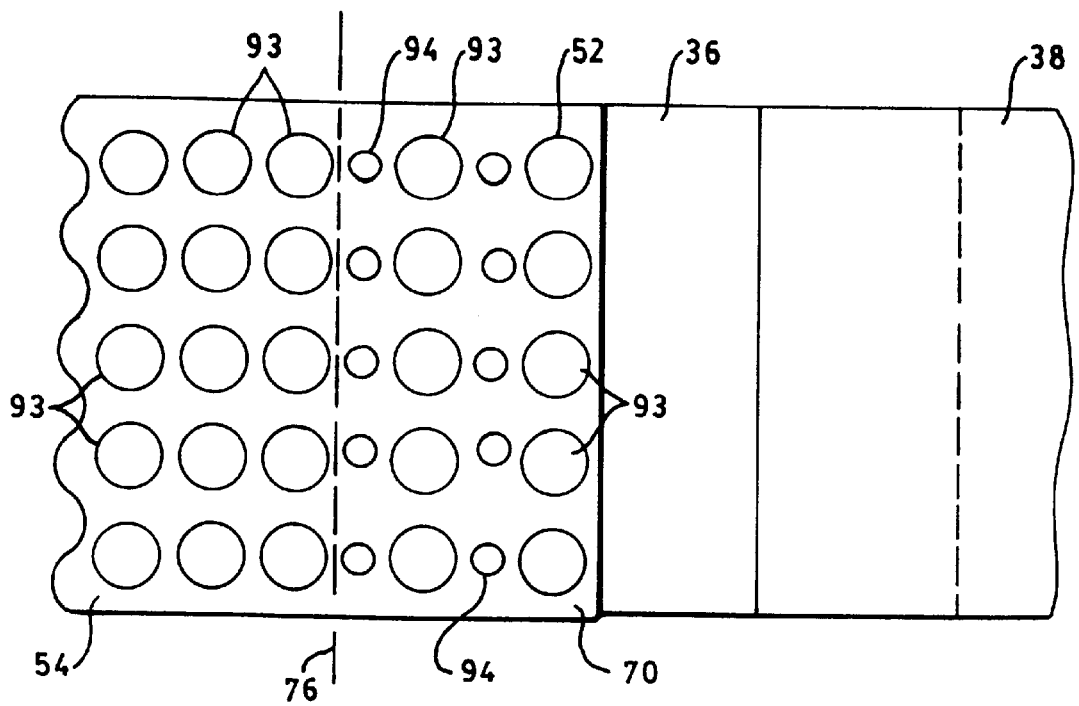
FIG. 14 representatively shows a schematic, top plan view of a fastener having a laterally inboard, first engagement section with a combination of attachment members and stalk members, and a laterally outboard, second engagement section with attachment members.
Figure 14A:
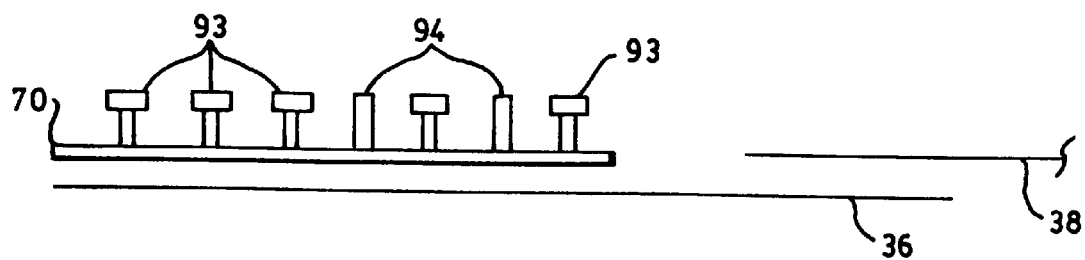
FIG. 14A representatively shows an expanded, schematic cross-sectional view of the fastener of FIG. 14.

With reference to FIGS. 14 and 14A, the first fastener component 70 can have a first, inboard engagement section 52 which includes a combination of stalk members 94 and attachment members 93. Additionally, the first fastener component can include an outboard engagement section 54 in which substantially 100% of the engagement members are attachment members 93. As a result, the fastening system can provide high, overall peel and shear force values while also providing a relatively high peel force value at the outboard engagement section 54 to provide increased resistance to disengagement.

Figure 15:
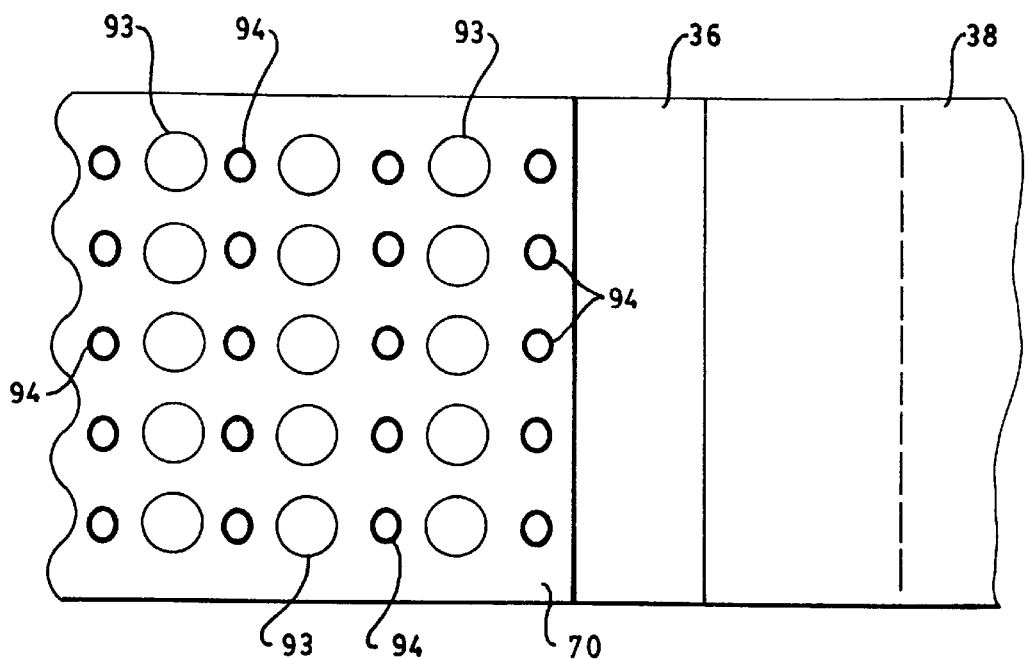
FIG. 15 representatively shows a schematic, top plan view of a fastener having a laterally inboard, first engagement section with relatively shorter stalk members, and a laterally outboard, second engagement section with relatively taller attachment members.
Figure 15A:
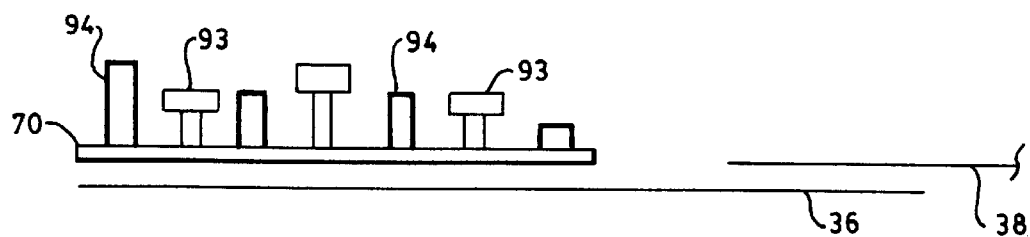
FIG. 15A representatively shows an expanded, schematic cross-sectional view of the fastener of FIG. 15.

With reference to FIGS. 15 and 15A, the first fastener component 70 can have a combination of attachment members 93 and stalk members 94. The attachment members may have differing heights, and the stalk members may have differing heights. Additionally, the heights of the stalk members 94 can be relatively taller or shorter than the heights of the attachment members 93, as desired.

Figure 16:
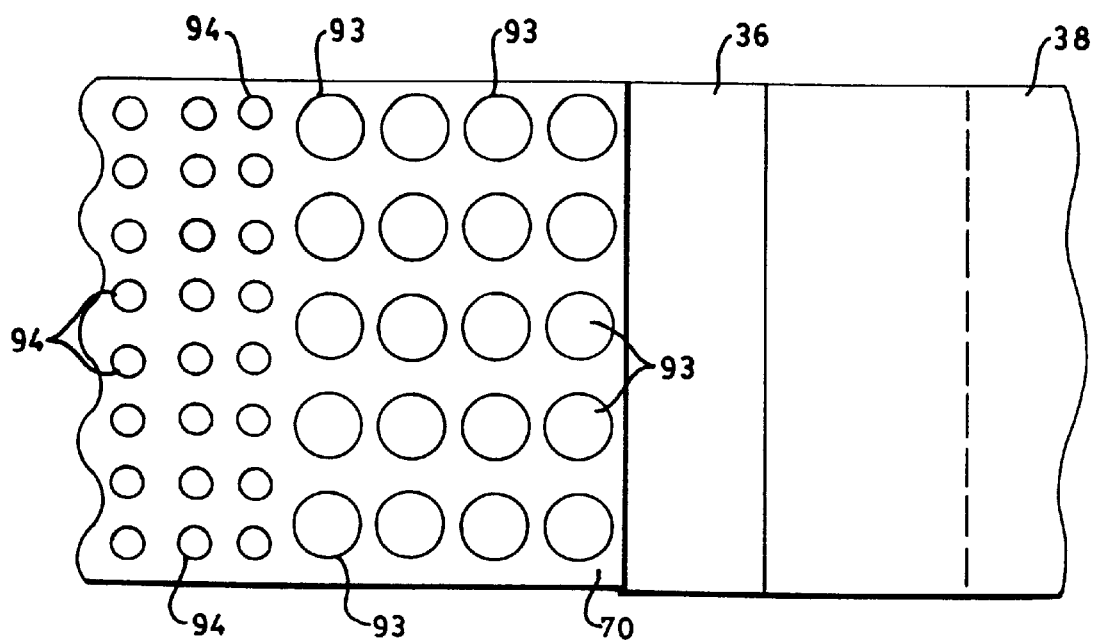
FIG. 16 representatively shows a schematic, top plan view of a fastener having a laterally inboard, first engagement section with relatively shorter attachment members, and a laterally outboard, second engagement section with relatively taller stalk members.
Figure 16A:
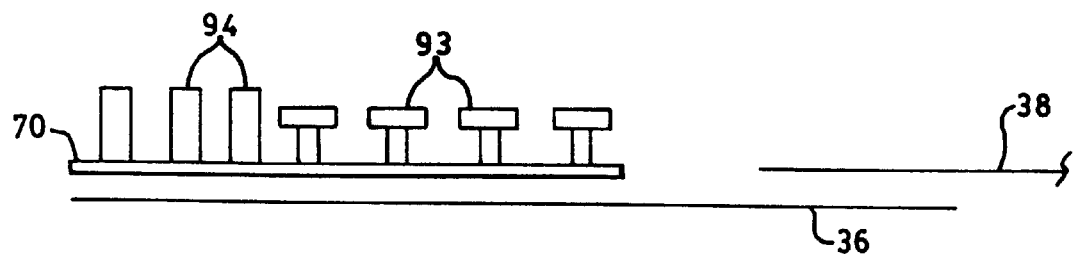
FIG. 16A representatively shows an expanded, schematic cross-sectional view of the fastener of FIG. 16.

With reference to FIGS. 16 and 16A, the first fastener component 70 can include another combination of attachment members 93 and stalk members 94. In this arrangement, substantially all of the stalk members 94 can have heights that are relatively greater than the heights of the attachment members 93. Optionally, substantially all of the stalk members 94 have heights that are relatively smaller than the heights of the attachment members 93.

Figure 17:
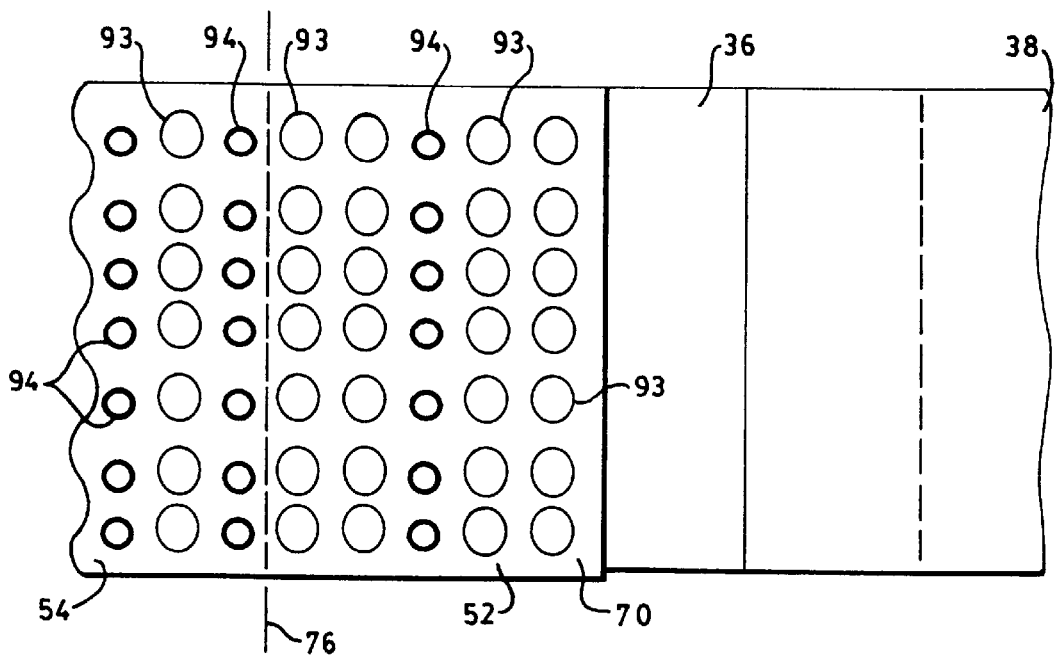
FIG. 17 representatively shows a schematic, top plan view of a fastener having a laterally inboard, first engagement section with a first concentration of attachment members and stalk members of selective heights, and a laterally outboard, second engagement section with a second concentration of attachment members and stalk members with different heights.
Figure 17A:
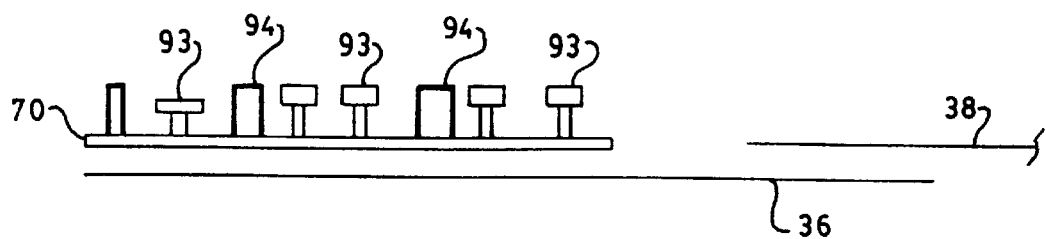
FIG. 17A representatively shows an expanded, schematic cross-sectional view of the fastener of FIG. 17.

With reference to FIGS. 17 and 17A, the first fastener component 70 can have a plurality of engagement sections with each engagement section having a combination of stalk members 94 and attachment members 93. In one engagement section the height of the stalk members 94 can be greater than the height of the attachment members 93. In another section, the height of the stalk members 94 can be equal to or less than the height of the attachment members 93 (e.g. FIGS. 15 and 15A).

Figure 18:
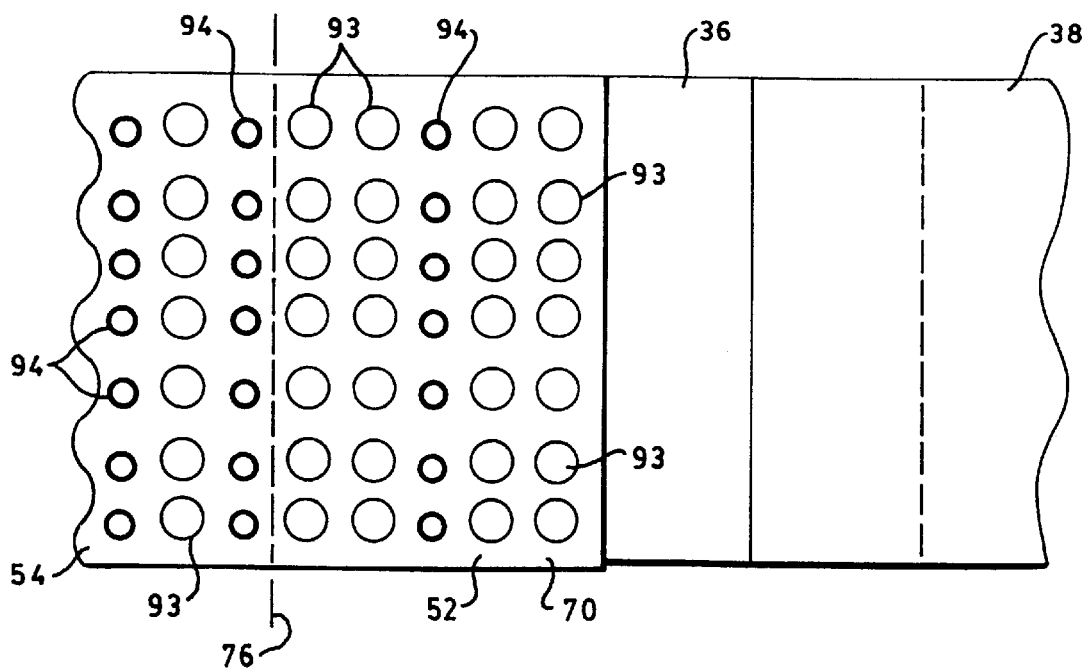
FIG. 18 representatively shows a schematic, top plan view of a fastener having a laterally inboard, first engagement section with a first combination composed of a first quantity of attachment members and a first quantity of stalk members, and a laterally outboard, second engagement section with a second combination composed of a second quantity of attachment members and a second quantity of stalk members.
Figure 18A:
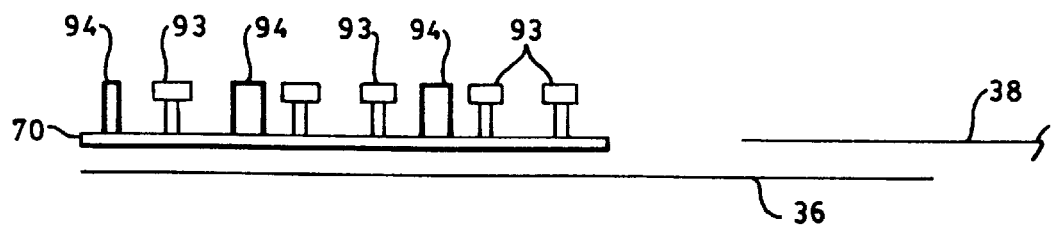
FIG. 18A representatively shows an expanded, schematic cross-sectional view of the fastener of FIG. 18.

With reference to FIGS. 18 and 18A, the first fastener component 70 can have a plurality of engagement sections, such as engagement sections 52 and 54. Each engagement section can include a different quantity of stalk members 94 and a different quantity of attachment members 93. One engagement section can have a greater number or quantity of stalk members 94 as compared to another engagement section. Similarly, one engagement section can include a greater number of attachment members 93 as compared to another engagement section. In addition, one engagement section can have a relatively higher concentration of stalk members 94 as compared to another engagement section, and one engagement section can have a relatively higher concentration of attachment members 93 as compared to another engagement section.

The various arrangements of the first fastener component may include a plurality of stalk members having substantially uniform width dimensions, or may include a plurality of stalk members having a combination of different width dimensions. In particular arrangements, for example, each engagement section can include stalk members having a selected width dimension or a selected combination of width dimensions, as representatively shown in FIGS. 17 through 20A. By employing a selected width dimension or combination of width dimensions, the stiffness and flexibility of the stalk members can be configured to help adjust the tactile feel of the first fastener component and to help adjust the shear force value or values provided by the fastener system.

Figure 19A:
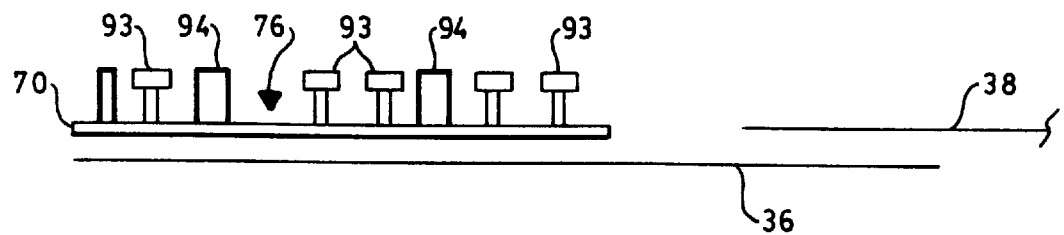
FIG. 19A representatively shows an expanded, schematic cross-sectional view of the fastener of FIG. 19.

With reference to FIGS. 19 and 19A, the first fastener component 70 can include first and second engagement sections 52 and 54 which are spaced apart by a transition zone 76 which provides a separation area 82 that is substantially free of engagement members. The separation area may also be substantially free of other protrusions.

With reference to FIGS. 20 and 20A, the first fastener component 70 can include two or more engagement sections 52, 54 and 96. Each of the engagement sections can have the configuration of a strip region which extends along the longitudinal direction 26 of the article. Additionally, each of the engagement sections can have a different combination of attachment members 93 and stalk members 94.

As representatively shown in FIGS. 19 and 20, at least an immediately adjacent pair of the engagement sections can have the configuration of longitudinally extending strip regions. In addition, the immediately adjacent pair of engagement sections can be spaced-apart by a fastener transition region 76 which includes a separation area 82 which is substantially free of the attachment members. In addition, the immediately adjacent pair of engagement sections can be spaced-apart by a separation area 82 which is substantially free of protrusions having a height of more than about 0.2 mm. In desired arrangements, the separation area 82 can provide a separation distance 84 which is not more than a maximum of about 20 mm. Alternatively, the separation distance can be not more than about 10 mm, and optionally, can be not more than about 3 mm to provide improved performance. The minimum separation distance can effectively be the selected distance between immediately adjacent attachment members.

In the various arrangements of the invention, the first plurality of stalk and/or attachment members in the first engagement section 52 can have a first arrangement pattern, and the appointed second plurality of stalk and/or attachment members in the second engagement section 54 can have a second arrangement pattern, with the second arrangement pattern differing from the first arrangement pattern.

In particular aspects, the first plurality of attachment members in the first engagement section can include a first distribution of non-isotropic hook members, and the second attachment section can include a second plurality of attachment members which includes a second distribution of non-isotropic hook members. Each non-isotropic hook member can have a stem portion 58 with a distal end region 44, and has a non-isotropic attachment element 60 disposed at the distal end region of its corresponding stem portion. The first distribution of non-isotropic hook members can have a first alignment pattern of their non-isotropic attachment elements, and the second distribution of non-isotropic hook members can have a second alignment pattern of their non-isotropic attachment elements. The second alignment pattern can differ from the first alignment pattern to provide a selected difference in the engagement forces generated by the first and second engagement sections.

In other aspects, the first plurality of attachment members 94 in the first engagement section 52 can include a first distribution of non-symmetric hook members, and the second plurality of attachment members in the second engagement section 54 can include a second distribution of non-symmetric hook members. Each non-symmetric hook member can have a stem portion 58 with a distal end region 44, and can have a non-symmetric attachment head element 60 disposed at the distal end region of its corresponding stem portion. The first distribution of non-symmetric hook members can have a first alignment pattern of their non-symmetric attachment elements, and the second distribution of non-symmetric hook members can have a second alignment pattern of their non-symmetric attachment elements. The second alignment pattern can differ from the first alignment pattern to provide a selected difference in the engagement forces generated in the first and second engagement sections 52 and 54, respectively. Examples of suitable arrangement patterns and alignment patterns are described in U.S. patent application Ser. No. 09/156,185 filed Sep. 17, 1998 and entitled MECHANICAL FASTENING SYSTEM HAVING SECTIONS WITH ARRANGED ENGAGEMENT MEMBERS by A. Longet al.

In the various configurations of the invention, the distribution patterns of the attachment members and the alignment patterns of the associated attachment elements and attachment openings are typically determined with respect to the first fastener component prior to its engagement to the appointed, complementary second fastener component. In desired aspects, the distribution patterns and alignment patterns are substantially maintained when the first and second fastener components are operatively inter-engaged. In addition, the individual attachment members are typically flexible and resilient, but will substantially retain their initial shape during ordinary use. When flexed or deformed during ordinary use, the attachment members will substantially avoid plastically deforming to sustain the deformation, and will, instead, substantially return or "spring-back" to their original orientations and shape.

Figure 21:
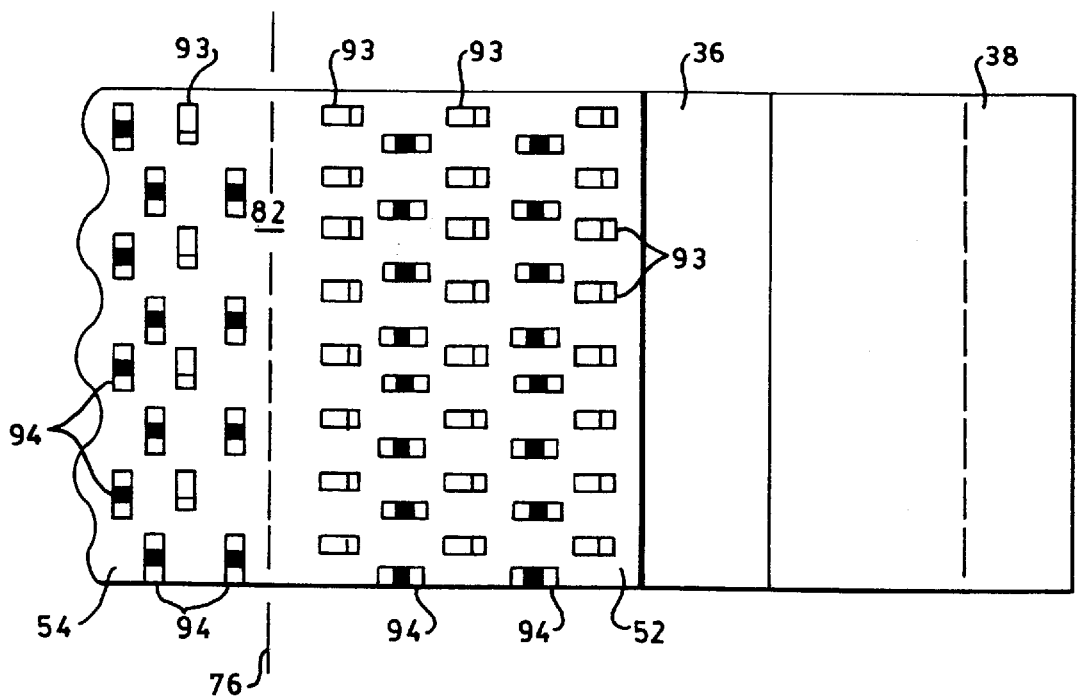
FIG. 21 representatively shows a schematic, top plan view of a fastener having a laterally inboard, first engagement section having a first combination of stalk members and non-symmetric, J-shaped attachment members arranged in a first alignment pattern, and a laterally outboard, second engagement section with a second combination of stalk members and J-shaped attachment members arranged in a second alignment pattern.
Figure 21A:
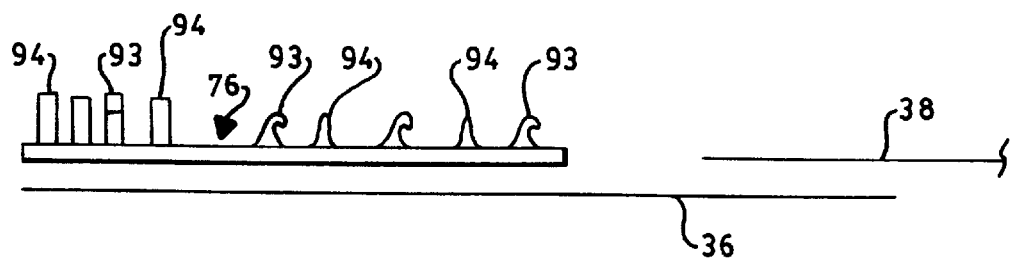
FIG. 21A representatively shows an expanded, schematic cross-sectional view of the fastener of FIG. 21.

With reference to FIGS. 21 and 21A, for example, the first fastener component 70 can include a plurality of engagement sections 52 and 54, and can include non-isotropic and non-symmetric attachment members 93. In one engagement section, the non-symmetric attachment members have a first alignment pattern, and in the other engagement section the attachment members have a second, different alignment pattern.

Figure 22:
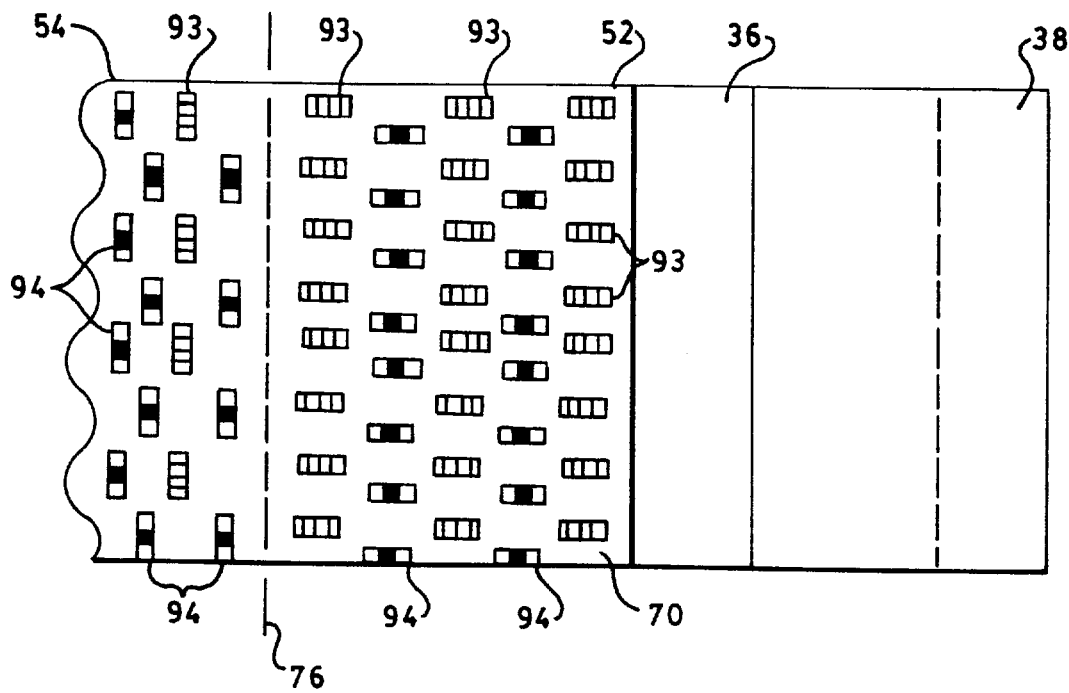
FIG. 22 representatively shows a schematic, top plan view of a fastener having a laterally inboard, first engagement section having a first combination of stalk members and non-isotropic, prong-type attachment members arranged in a first alignment pattern, and a laterally outboard, second engagement section with a second combination of stalk members and prong-type attachment members arranged in a second alignment pattern.
Figure 22:
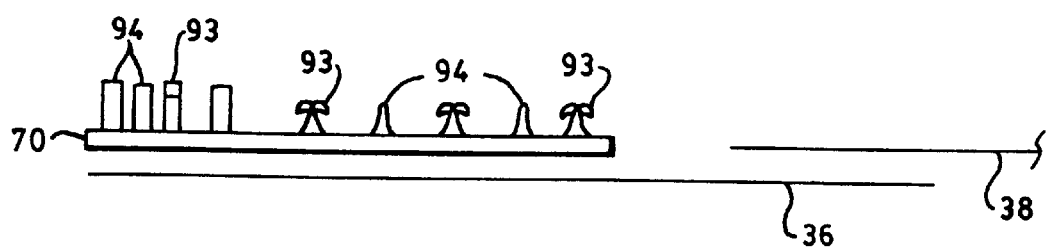

With reference to another example representatively shown in FIGS. 22 and 22A, the first fastener component 70 can include a plurality of engagement sections 52 and 54 which include non-isotropic attachment members 93. In the representatively shown configuration, the non-isotropic attachment members do have bilateral symmetry. In one engagement section such as the inboard engagement section 52, the attachment members have a first alignment pattern, and in another engagement section, such as the outboard engagement section 54, the attachment members 93 have a second alignment pattern.

Figure 23:
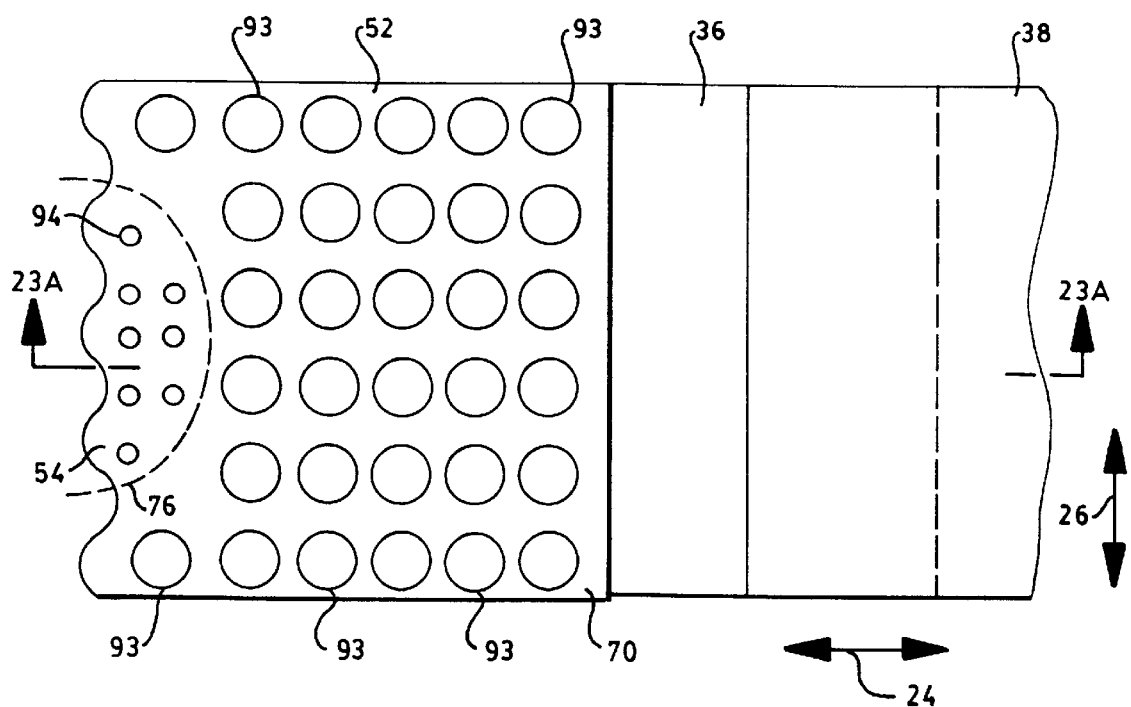
FIG. 23 representatively shows a schematic, top plan view of a fastener having a first engagement section having a distribution of attachment members, and a generally crescent shaped, second engagement section having a distribution of stalk members.
Figure 23A:
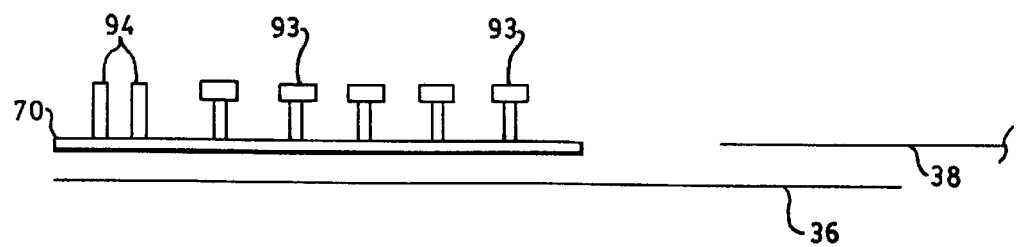
FIG. 23A representatively shows an expanded, schematic cross-sectional view of the fastener of FIG. 23.

With reference to FIGS. 23 and 23A, the boundaries of the various engagement sections of the first fastener component may have one or more non-rectilinear configurations. The representatively shown arrangement, for example, has a generally crescent shaped second engagement section 54 that is positioned along a laterally outboard edge region of the first engagement section 52. The shown arrangement has the second engagement section approximately centered along the longitudinal direction 26 of the fastener. Optionally, the second engagement section may be non-centered along the longitudinal direction. Accordingly, the area of the second engagement section 54 is indented into the area of the first engagement section 52. The second engagement section contains a higher proportion of stalk members 94, as compared to the first engagement section, and in the shown arrangement, the second engagement section contains approximately 100% stalk members. As a result, the second engagement section 54 can thereby provide an area along the laterally outboard, distal edge of the fastener that has a relatively low peel force engagement. The low peel force region can provide a convenient finger-grip, lift region which can be readily located, lifted and grasped to detach the fastener tab.

Where the first fastener component 70 or a particular engagement section 52 or 54 has a relatively higher quantity or concentration of stalk members 94, the first fastener component or the particular engagement section, can provide an increased shear force value without excessively increasing the associated peel force value. In examples of the various configurations of the invention, the first engagement section 52 can include a first plurality of engagement members 56 having a first quantity of engageable stalk members 94, and the second engagement section 54 can include a second plurality of engagement members having a second quantity of engageable stalk members (e.g. FIGS. 18 and 18A). In desired arrangements, the second quantity of stalk members differs from the first quantity of stalk members. In more particular arrangements, the second quantity of stalk members can be greater or less than the first quantity of stalk members. The first plurality of engagement members in the first engagement section 52 can provide a first concentration of stalk members per unit area, and the second plurality of engagement members in the second engagement section 54 can provide a second concentration of stalk members per unit area.

The second concentration of stalk members can differ from the first concentration of stalk members to provide a selected difference in the engagement shear forces generated in the first and second engagement sections 52 and 54, respectively. In particular configurations the first concentration of stalk members is greater than the second concentration of stalk members, and the engagement shear force generated in the first engagement section 52 is relatively greater than the engagement shear force generated in the second engagement section 54. Optionally, the first concentration of stalk members in the first engagement section 52 can be substantially equal to or less than the second concentration of stalk members in the second engagement section 54. Accordingly, the engagement shear force in the first engagement section 52 can be substantially equal to or less than the engagement shear force generated in the second engagement section 54.

Similarly, the first plurality of engagement members in the first engagement section 52 can provide a first concentration of attachment members 93 per unit area, and the second plurality of engagement members in the second engagement section 54 can provide a second concentration of attachment members 93 per unit area. The second concentration of attachment members can differ from the first concentration of attachment members to provide a selected difference in the engagement peel forces generated in the first and second engagement sections 52 and 54, respectively. In particular configurations, the first concentration of attachment members is greater than the second concentration of attachment members, and the engagement peel force generated in the first engagement section 52 is relatively greater than the engagement peel force generated in the second engagement section 54. Optionally, the first concentration of attachment members in the first engagement section 52 can be substantially equal to or less than the second concentration of attachment members in the second engagement section 54. Accordingly, the engagement peel force in the first engagement section 52 can be substantially equal to or less than the engagement peel force generated in the second engagement section 54.

In still other aspects, the first plurality of engagement members 56 can include the first quantity of engageable stalk members 94 combined with a first quantity of attachment members 93. Additionally, the second plurality of engagement members can include the second quantity of engageable stalk members combined with a second quantity of attachment members. Accordingly, the first engagement section 52 can provide a first combination of securement shear force and securement peel force, and the second engagement section 54 can provide a second combination of such shear and peel forces.

In particular aspects, the peel force value provided by the second engagement section 54 can be equal to or greater than the peel force value provided by the first engagement section 52. In still further aspects, the peel force value provided by the second engagement section 54 can be greater than zero, and less than the peel force value provided by the first engagement section 52. In a desired example, the first plurality of engagement members in the first engagement section 52 can provide a high peel force value and a low shear force value, and the second plurality of engagement members in the second engagement section 54 can provide a relatively lower peel force value and a relatively higher shear force value. As a result, the fastening system can provide a strong, reliable fastening system for use, while also providing an end edge region that is easy to locate and lift for any desired disengagement.

The first peel force value provided by the first engagement section 52 can, for example, be at least about 16 grams-force per centimeter of engagement width (16 gmf/cm). Alternatively, the first peel force value can be at least about 80 gmf/cm, and optionally, can be at least about 160 gmf/cm to provide improved performance. In further aspects, the first peel force value can be not more than a maximum of about 470 gmf/cm. The first peel force value may alternatively be not more than about 315 gmf/cm, and optionally may be not more than about 240 gmf/cm to provide further benefits.

Additionally, the second peel force value provided by the second engagement section 54 can be at least about 5% of the first peel force value. The second peel force value can alternatively be at least about 10%, and optionally, can be at least about 15% of the first peel force value to provide improved benefits. In other aspects, the second peel force value can be not more than about 100% of the first peel force value. The second peel force value alternatively be not more than about 50%, and optionally, can be not more than about 25% of the first peel force value to provide improved performance.

In another aspect of the invention, The first engagement section 52 can include a first quantity of attachment members having a first combination of hook styles. Additionally, the second engagement section 54 can include a second quantity of attachment members having a second combination of hook styles.

In the various arrangements of the invention, the attachment members of each of the first and second engagement sections 52 and 54 can be formed or otherwise provided on substantially a single, unitary piece of the substrate layer 110. Thus, the appointed region of the substrate layer employed for the first engagement section 52 can be substantially contiguous with the appointed region of the substrate layer employed for the second engagement section 54. Alternatively, the attachment members of the first and second engagement sections 52 and 54 can be formed or otherwise provided on individual, separately provided sections or pieces of desired substrate layer materials.

The various arrangements of the invention can include a fastener transition region 76 located between selected engagement sections (e.g. FIGS. 9 and 19). The transition region may be configured to extend along any operative direction. For example, the transition region 76 may be positioned between laterally adjacent regions of the first and second engagement sections 52 and 54, and may be configured to extend substantially lengthwise along the longitudinal direction 26 of the article.

In the various configurations of the invention, the desired demarcations or transition regions between the appointed engagement sections (e.g. between the engagement sections 52 and 54) can be abrupt or gradual. For example, adjacent engagement sections can be configured as distinct and separate area sections of the fastener component. The engagement sections can be abruptly and sharply delineated by a distinct line, space or other region of generally discontinuous separation, as representatively shown in the various Figures. Alternatively, the engagement sections can be gradually delimited by an interconnecting transition region wherein one or more of the desired structures or parameters of the individual engagement sections may continuously or continually change, in a substantially gradient manner, as one moves from one engagement section to another, adjacent engagement section. In additional aspects, the first fastener component 70 can include a first engagement section 52 having a first plurality of attachment members 56 which provide a first, attachment member (e.g. hook) height value, and a second engagement section 54 having a second plurality of attachment members which provide a second, attachment member (e.g. hook) height value. The second height value differs from the first height value, and in a particular aspect, the second height value can be configured to be less than the first height value. In other aspects, the second height value can be configured to be greater than the first height value. In particular configurations, the relatively shorter attachment members that are disposed in and distributed over selected areas can help reduce the engagement force in the selected areas. In other configurations, the relatively shorter attachment members that are disposed in and distributed over selected areas can help reduce redmarking and/or skin irritation. Such advantages can, for example, arise from having the attachment elements located and held at a position that is relatively closer to the base substrate layer and farther from the wearer's skin. Examples of fastening systems having attachment members with different heights are shown and described in U.S. patent application Ser. No. 09/348,860 entitled MECHANICAL FASTENING SYSTEM HAVING ENGAGEMENT MEMBERS WITH SELECTED HEIGHTS by B. Nortman et al. and filed Jul. 7, 1999; the entire disclosure of which is incorporated herein by reference in a manner that is consistent herewith.

For the various configurations of the invention, an example of a suitable attachment hook member is a micro-hook member provided in a material which is distributed under the designation VELCRO HTH 829, and is available from VELCRO U.S.A., Inc., a business having offices in Manchester, N.H. The micro-hook material has attachment members in the shape of angled, prong-type hook members. The hook members can be configured with a hook height which is within the range of about 0.030–0.063 cm (about 0.012–0.025 inch); and a hook width which is within the range of about 0.007 to 0.022 cm (about 0.003 to 0.009 inch). The hook elements are molded onto a base layer substrate having a thickness of about 0.0076–0.008 cm (about 0.003–0.0035 inch), and the hook material has a Gurley stiffness of about 12 mgf (about 12 Gurley units). Other suitable hook members can be found on VELCRO HTH 858, VELCRO HTH 851 and VELCRO HTH 863 hook materials. Another suitable type of attachment hook member can be found on a 3M CS 200 material available from the 3M Company, a business having offices in St. Paul, Minn.

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various configurations of the invention, the loop material can be provided by a nonwoven, woven or knit fabric, as well as combinations thereof. For example, a suitable loop material fabric can be composed of a 2 bar, warp knit fabric of the type available from Guilford Mills, Inc., Greensboro, N.C. under the trade designation #34285, as well as other types of knit fabrics. Suitable loop materials are also available from the 3M Company, which has distributed a nylon woven loop under their SCOTCHMATE brand. The 3M Company has also distributed a liner-less loop web with adhesive on the backside of the web, and 3M knitted loop tape.

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., which issued Jan. 12, 1999 the entire disclosure of which is incorporated herein by reference in a manner that is consistent herewith.

The loop material employed in the various configurations of the invention need not be limited to a discrete or isolated patch on the outward surface of the article. Instead, the loop material can be provided by a substantially continuous, outer fibrous layer which is assembled, integrated or otherwise joined to extend over a predetermined surface area of the desired article. For example, the outer fibrous layer may be arranged to extend over substantially the total exposed surface area of a cloth-like outer cover employed with the article.

In the various configurations of the invention, the engagement force between the selected first fastener component and its appointed and cooperating second fastener component should be large enough and durable enough to provide an adequate securement of the article on the wearer during use. In particular arrangements, especially where there are sufficiently high levels of engagement shear force provided by the fastening system, the fastening engagement may provide a peel force value of not less than a minimum of about 40 grams-force (gmf) per inch (16 gmf/cm) of the "width" of engagement between the first and second fastener components. In further arrangements, the fastening engagement may provide a peel force value of not less than about 100 gmf/inch (39 gmf/cm) to provide improved advantages. In desired configurations, the fastening engagement may provide a peel force value of not less than about 200 gmf per inch (80 gmf/cm) of the "width" of engagement between the first and second fastener components. Alternatively, the peel force is not less than about 300 gmf/inch (118 gmf/cm), and optionally is not less than about 400 gmf/inch (160 gmf/cm) to further provide improved benefits. In other aspects, the peel force is not more than about 1,200 gmf/inch (470 gmf/cm). Alternatively, the peel force is not more than about 800 gmf/inch (315 gmf/cm), and optionally is not more than about 600 gmf/inch (240 gmf/cm) to provide improved performance.

The engagement force between the selected first fastener component and its appointed and cooperating second fastener component may additionally provide a shear force value of not less than about 400 gmf per square inch (62 gmf/cm$^2$) of the area of engagement between the first and second fastener components. Alternatively, the shear force is not less than about 1,000 gmf/in$^2$ (155 gmf/cm$^2$), and optionally, is not less than about 1,700 gmf/in$^2$ (264 gmf/cm$^2$). In further aspects, the shear force can be up to about 4,400 gmf/in$^2$ (682 gmf/cm$^2$), or more. Alternatively, the shear force is not more than about 3,900 gmf/in$^2$ (604 gmf/cm$^2$), and optionally is not more than about 3,500 gmf/in$^2$ (542 gmf/cm$^2$) to provide improved performance.

For the various configurations of the invention, the peel force value can be determined in accordance with standard procedure ASTM D5170, approved Sep. 15, 1991 and published November 1991; with the following particulars. The test specimen is the fastener tab from the article being assessed. The test specimen length is the dimension aligned along the direction in which a peel-away force is typically applied to disengage and remove the fastener during the ordinary use of the article with which the fastener is employed. The specimen "Width" lies within the general plane of the fastener and is perpendicular to the specimen length. The roller device weighs 4.5 pounds (2.05 kg) and includes a rubber coating around the roller circumference. A suitable roller is part number HR-100 available from Chemsultants International, a business having a location in Mentor, Ohio During the engagement of the fastener components, the roller is rolled over the test specimen through one cycle in the direction of the cross-wise "width" of the sample. In addition, the initial peel by hand to "raise the loops" is omitted. During testing, the fastener material held by the stationary clamp can be larger in area, as compared to the fastener material held in the moving clamp. The initial separation distance between the clamps of the tensile tester is 4 inch (10.2 cm), and the extension speed of the tensile testing machine is 20 inch/min (50.8 cm/min). The reported value of a peel test result is a "three-peak average" value employing MTS TESTWORKS software with a peak criteria of 2%. Additionally, the peel force value is normalized to be stated in terms of force per unit length of the "width" dimension of the fastener component on the test specimen, such as grams per inch or grams per centimeter. The MTS TESTWORKS software is available from MTS Systems Corporation, a business having offices in Eden Prairie, Minn.

The shear force value can be determined in accordance with the standard procedure ASTM D-5169, approved Sep. 15, 1991 and published Nov. 1991 with the following particulars. The test specimen is composed of the fastener tab from the article being assessed. The test specimen length and width typically correspond to the length and width employed to conduct the testing for peel force value. Ordinarily, the test specimen length is the dimension aligned along the direction in which a shear force is typically applied to the fastener during the ordinary use of the article with which the fastener is employed. The specimen "width" lies within the general plane of the fastener and is perpendicular to the specimen length. The roller device weighs 4.5 pounds (2.05 kg) and includes a rubber coating around the roller. A suitable roller is part number HR-100 available from Chemsultants International, a business having a location in Mentor, Ohio During the engagement of the fastener components, the roller is rolled over the test specimen through five cycles in the direction of the cross-wise "width" of the sample. In addition, the initial peel by hand to "raise the loops" is omitted. During testing, the fastener material (e.g. the loop material) held by the stationary clamp can be larger in area, as compared to the fastener material (e.g. hook material) held in the moving clamp. The initial separation distance between the clamps of the tensile tester is 4 inch (10.2 cm), and the extension speed of the tensile testing machine is 10 inch/min (25.4 cm/min). The shear force value is normalized to be stated in terms of force per unit area of the test specimen, such as grams-force per inch$^2$ (or gmf/cm$^2$).

The particulars of the standard test procedures are intended to generate fastening conditions that can be more representative of consumer use conditions. When preparing the test specimen materials (e.g. hook and loop materials) to determine the cooperating peel and/or shear force values for the representatively shown configurations of the invention, it should be noted that, the width dimension of the selected specimen material will correspond to the dimension of the fastener material which, in the actual article, is found to be aligned along the longitudinal direction 26 of the article. Similarly, the length dimension of the selected specimen material will correspond to the dimension of the fastener material which, in the actual article, is found to be aligned along the lateral direction 24 of the article.

Desirably, the securing engagement between the first and second fastener components should be sufficient to prevent a disengagement of the fastener tab 36 away from the landing member 50 when the fastener tab 36 is subject to a tensile shear force of at least about 1,000 grams when the tensile force is applied outwardly along the lateral direction, aligned generally parallel with the plane of the backsheet layer 30 of the article.

Each of the fastener components and fastening elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with their associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An article having a longitudinal direction, a lateral cross-direction, a first article portion, a second article portion, and a fastener for securing said first article portion to said second article portion, said fastener including:
   at least one first fastener component attached to said first portion of the article; and
   a cooperating, second fastener component, which is mechanically engageable with said first fastener component and is attached to said second portion of the article;
   wherein
   said first fastener component includes a first engagement section, and a second engagement section which is located laterally outboard from said first engagement section;
   said first engagement section includes a first plurality of engagement members having a first quantity of engageable stalk members with a number of engageable stalk members that is not more than about 35% of a total number of engagement members in said first fastener component;
   said second engagement section includes a second plurality of engagement members having a different, second quantity of engageable stalk members with a number of engageable stalk members that is at least about 5% of the total number of engagement members in said first fastener component;
   each said stalk member has a stalk length, a minimum stalk width and a distal end portion with each said distal end portion having a maximum end-span which is not more than 130% of said minimum stalk width;
   said first engagement section is configured to provide a first peel force value, and
   said second engagement section is configured to provide a second peel force value that is less than said first peel force value.

2. An article as recited in claim 1, wherein
   said first plurality of engagement members includes said first quantity of engageable stalk members combined with a first quantity of attachment members having attachment elements; and
   said second plurality of engagement members includes said different, second quantity of engageable stalk members combined with a second quantity of attachment members having attachment elements.

3. An article as recited in claim 2, wherein
   said first plurality of engagement members includes said first quantity of engageable stalk members combined with a first quantity of attachment members having hook elements; and
   said second plurality of engagement members includes said second quantity of engageable stalk members combined with a second quantity of attachment members having hook elements.

4. An article as recited in claim 3, wherein said attachment hook elements include mushroom-cap elements.

5. An article as recited in claim 2, wherein said attachment members provide an average hook height value, and said stalk members provide an average stalk height value which is at least about 10% of said average hook height value.

6. An article as recited in claim 2, wherein
   said first plurality of attachment members includes a first distribution of non-isotropic hook members, and said second plurality of attachment members includes a second distribution of non-isotropic hook members;
   each non-isotropic hook member has a stem portion with a distal end region, and has a non-isotropic attachment element disposed at said distal end region of its corresponding stem portion;
   said first distribution of non-isotropic hook members has a first alignment pattern of their non-isotropic attachment elements; and
   said second distribution of non-isotropic hook members has a second alignment pattern of their non-isotropic attachment elements, with said second alignment pattern differing from said first alignment pattern.

7. An article as recited in claim 2, wherein
   said first plurality of attachment members includes a first distribution of non-symmetric hook members, and said second plurality of attachment members includes a second distribution of non-symmetric hook members;
   each non-symmetric hook member has a stem portion with a distal end region, and has a non-symmetric attachment head element disposed at said distal end region of its corresponding stem portion;

said first distribution of non-symmetric hook members has a first alignment pattern of their non-symmetric attachment elements; and said second distribution of non-symmetric hook members has a second alignment pattern of their non-symmetric attachment elements, with said second alignment pattern differing from said first alignment pattern.

8. An article as recited in claim 2, wherein said first plurality of attachment members have a first attachment member height value; and said second plurality of attachment members have a second attachment member height value which is less than said first attachment member height value.

9. An article as recited in claim 1, wherein said second fastener component includes a loop material.

10. An article as recited in claim 1, wherein said first and second engagement sections have the configuration of longitudinally extending strip regions.

11. An article as recited in claim 1, wherein said distal end portion of each said stalk member has a maximum end-span which is not more than 115% of said stalk width.

12. An article as recited in claim 1, wherein said distal end portion of each said stalk member has a maximum end-span which is not more than 104% of said stalk width.

13. An article as recited in claim 1, wherein said stalk members have a minimum stalk height which is at least of about 0.025 cm.

14. An article as recited in claim 1, wherein said first plurality of engagement members provide a first concentration of stalk members per unit area, and said second plurality of engagement members provide a different, second concentration of stalk members per unit area.

15. An article as recited in claim 14; wherein said first concentration of stalk members is less than said second concentration of stalk members.

16. An article having a longitudinal direction, a lateral cross-direction, a first article portion, a second article portion, and a fastener for securing said first article portion to said second article portion, said fastener including:

at least one first fastener component attached to said first portion of the article; and a cooperating, second fastener component, which is mechanically engageable with said first fastener component and is attached to said second portion of the article;

wherein said first fastener component includes a first engagement section, and a second engagement section which is located laterally outboard from said first engagement section;

said first engagement section includes a first plurality of engagement members having a first quantity of engageable stalk members and a first quantity of attachment members with attachment hook elements, with a number of attachment members that is not more than about 95% of a total number of engagement members in said first fastener component;

said second engagement section includes a second plurality of engagement members having a second quantity of engageable stalk members and a second quantity of attachment members with attachment hook elements, with a number of attachment members that is at least about 15% of the total number of engagement members in said first fastener component;

said first plurality of engagement members provide a first concentration of attachment members per unit area of said first engagement section, and said second plurality of engagement members provide a second concentration of attachment members per unit area of said second engagement section which is greater than said first concentration of attachment members in said first engagement section;

each said stalk member has a stalk length, a minimum stalk width and a distal end portion with each said distal end portion having a maximum end-span which is not more than 130% of said minimum stalk width;

said first engagement section is configured to provide a first peel force value; and said second engagement section is configured to provide a second peel force value that is greater than said first peel force value.

17. An article as recited in claim 16, wherein said attachment hook elements include mushroom-cap elements.

18. An article as recited in claim 17, wherein said second fastener component includes a loop material.

19. An article as recited in claim 16, wherein said distal end portion of each said stalk member has a maximum end-span which is not more than 115% of said stalk width.

20. An article as recited in claim 16, wherein said distal end portion of each said stalk member has a maximum end-span which is not more than 104% of said stalk width.

* * * * *